United States Patent [19]

Sachs et al.

[11] Patent Number: 5,624,823
[45] Date of Patent: Apr. 29, 1997

[54] DNA ENCODING PROCINE INTERLEUKIN-10

[75] Inventors: David H. Sachs; Christian A. Leguern, both of Newton; Megan Sykes, Charlestown; Gilles J.F. Blancho, Cambridge, all of Mass.

[73] Assignee: The General Hospital Corporation, Boston, Mass.

[21] Appl. No.: 114,072

[22] Filed: Aug. 30, 1993

Related U.S. Application Data

[63] Continuation-in-part of Ser. No. 797,555, Nov. 22, 1991, abandoned, and a continuation-in-part of Ser. No. 838,595, Feb. 19, 1992, abandoned, and a continuation-in-part of Ser. No. 63,171, May 17, 1993, abandoned, and a continuation-in-part of Ser. No. 62,946, May 17, 1993, abandoned, said Ser. No. 838,595, is a continuation-in-part of Ser. No. 817,761, Jan. 8, 1992, abandoned, said Ser. No. 63,171, is a continuation-in-part of Ser. No. 838,595, and Ser. No. 797,555, said Ser. No. 62,946, is a continuation-in-part of Ser. No. 838,595.

[51] Int. Cl.$^6$ .............................. C12N 5/10; C12N 15/24
[52] U.S. Cl. ......................... 435/69.52; 435/320.1; 435/252.3; 435/365.1; 435/325; 536/23.5
[58] Field of Search ..................... 536/23.5; 435/320.1, 435/69.1, 252.3, 69.52, 240.2

[56] References Cited

U.S. PATENT DOCUMENTS 5,231,012  7/1993  Mosmann et al. ................ 435/69.52

OTHER PUBLICATIONS

Haynes et al., (1989) "The Role of Leukocyte Adhesion Molecules in Cellular Interactions: Implications for the Pathogenesis of Inflammatory Synovitis"; vol. 11, pp. 163–185.
Fischel, et al., (1991) "Prolonged Survival of a Discordant Cardiac Xenograft in a Rhesus Monkey," Transplantation Proceedings, vol. 23, No. 1, pp. 589–590, Feb. 1991.
Sachs, et al. "Human Immunology of Xenogaft Rejection" Human Immunology; vol. 28, pp. 245–251; 1990.
Wee, et al, (1992) "The Effects of OKT4A Monoclonal Antibody on Cellular Immunity of nonhuman primate renal allografts recipients" Transplantations, vol. 53, pp. 501–507, Mar. 1992.
Reeck et al. 1987. Cell 50:667.
Lewin. 1987 Science 237:1570.
Bowie et al. 1990. Science 247:1306–1310.
Abramowicz et al., "Neonatal Induction of Transplantation Tolerance in Mice is Associated With In Vivo Expression of IL–4 and –10 mRNAs" Transplantation Proceedings, vol. 25, No. 1, pp. 312–313, Feb. 1993.
Takeuchi et al., "Heart Allografts In Murine Systems. The Differential Activation of Th2–like Effector Cells in Peripheral Tolerance" Transplantation, vol. 53, No. 6, pp. 1281–1294, Jun. 1992.

Merville et al., "Detection of Single Cells Secreting IFN–Gamma, IL–6, and IL–10 in Irreversible Rejected Human Kidney Allografts, and Their Modulation by IL–2 and IL–4" Transplantation, vol. 55, No. 3, pp. 639–646, Mar. 1993.
Moore et al., "Interleukin–10" Annu. Rev. Immunol., vol. 11, pp. 165–190, 1993.
Howard et al., "Interleukin 10 Protects Mice from Lethal Endotoxemia" J. Exp. Med., vol. 177, pp. 1205–1208, Apr. 1993.
Ishida et al., "Continuous Anti–Interleukin 10 Antibody Administration Depletes Mice of Ly–1 B Cells but Not Conventional B Cells" J. Exp. Med., vol. 175, pp. 1213–1220, May 1992.
Hsieh et al., "Development of $T_H1$ CD4$^+$T Cells Through IL–12 Produced by Listeria–Induced Macrophages" Science, vol. 260, pp. 547–549, Apr. 23, 1993.
Macatonia et al., "Dendritic cells and macrophages are required for Th1 development of CD4$^+$T Cells from αβ TCR transgenic mice: IL–12 substitution for macrophages to simulate IFN–γProduction is IFNγ–dependent" International Immunology, vol. 5, No. 9, pp. 1119–1128, 1993.
Macatonia et al., "Differential Effect of IL–10 on Dendritic Cell–Induced T Cell Proliferation and IFN–γ Production" The Journal of Immunology, vol. 150, No. 9, pp. 3755–3765, May 1, 1993.
Fiorentino et al., "IL–10 Inhibits Cytokine Production by Activated Macrophages" The Journal of Immunology, vol. 147, No. 11, pp. 3815–3822, Dec. 1, 1991.
Fiorentino et al., "Two Types of Mouse T Helper Cell. IV. Th2 Clones Secrete a Factor that Inhibits Cytokine Production by Th1 Clones" J. Exp. Med., vol. 170, pp. 2081–2095, Dec. 1989.
Moore et al., "Homology of Cytokine Synthesis Inhibitory Factor (IL–10) to the Epstein–Barr Virus Gene BCRFI" Science, vol. 248, pp. 1230–1234, Jun. 8, 1990.
Viera et al., "Isolation and expression of human cytokine synthesis inhibitory factor cDNA clones: Homology to Epstein–Barr virus open reading frame BCRFI" Proceedings of the National Acadamy of Sciences, vol. 88, pp. 1172–1176, Feb. 1991.
Fernandez–Botran et al., "Lymphokine–mediated Regulation of the Proliferative Response of Clones of T Helper 1 and T Helper 2 Cells" J. Exp. Med., vol. 168, pp. 543–558, Aug. 1988.
Fiorentino et al., "IL–10 Acts on the Antigen–presenting Cell to Inhibit Cytokine Production by Th1 Cells" The Journal of Immunology, vol. 146, No. 10, pp. 3444–3451, May 1991.

(List continued on next page.)

*Primary Examiner*—Stephen G. Walsh
*Assistant Examiner*—Elizabeth C. Kemmerer
*Attorney, Agent, or Firm*—Louis Myers, Ph.D.; Lahive & Cockfield

[57] ABSTRACT

Purified DNA encoding porcine IL–10, porcine IL–10, and methods of inducing immunological tolerance and inhibiting graft versus host disease.

27 Claims, 3 Drawing Sheets

OTHER PUBLICATIONS

Howard et al., "Biological properties of interleukin 10" *Immunology Today*, vol. 13, No. 6, pp. 198–200, 1992.

Feng et al., "Molecular Cloning of Rat Cytokine Synthesis Inhibitory Factor (IL–10) cDNA and Expression in Spleen and Macrophages" *Biochemical and Biophysical Research Communications*, vol. 192, No. 2, pp. 452–458, Apr. 30, 1993.

De Waal Malefyt et al., "Interleukin 10(IL–10) Inhibits Cytokine Synthesis by Human Monocytes: An Autoregulatory Role of IL–10 Produced by Monocytes" *J. Exp. Med.*, vol. 174, pp. 1209–1220, Nov. 1991.

Cherwinski et al., "Two Types of Mouse Helper T Cell Clone. III. Further Differences in Lymphokine Synthesis between Th1 and Th2 Clones Revealed by RNA Hybridization, Functionally Monospecific Bioassays, and Monoclonal Antibodies" *J. Exp. Med.*, vol. 166, pp. 1229–1244, Nov. 1987.

Horowitz et al., "Autocrine growth inhibition of a cloned line of helper T cells" *Proceedings of the National Academy of Sciences*, vol. 83, pp. 1886–1890, Mar. 1986.

Mosmann et al., "Two Types of Murine Helper T Cell Clone I. Definition According to Profiles of Lymphokine Activities and Secreted Proteins" *The Journal of Immunology*, vol. 136, No. 7, pp. 2348–2357, Apr. 1, 1986.

Gajewski et al., "Anti–proliferative Effect of IFN–$\gamma$ in Immune Regulation. I. IFN–$\gamma$ Inhibits the Proliferation of Th2 but Not Th1 Murine Helper T Lymphocyte Clone" *The Journal of Immunology*, vol. 140, No. 12, pp. 4245–4252, Jun. 15, 1988.

Del Prete et al., "Human IL–10 is Produced by Both Type 1 Helper (Th1) and Type 2 Helper (Th2) T Cell Clones and Inhibits Their Antigen–Specific Proliferation and Cytokine Production" *The Journal of Immunology*, vol. 150, No. 2, pp. 353–360, Jan. 15, 1993.

O'Garra et al., "Production of cytokines by mouse B cells: B lymphomas and normal B cells produce interleukin 10" vol. 2, No. 9, pp. 821–832, 1990.

FIG. 1

SEQ ID NO: 1

DNA ENCODING PROCINE INTERLEUKIN-10

This invention was made with Government support under Contract #HL 18646 and AI 33053 awarded by the National Institutes of Health. The Government has certain rights in this invention.

BACKGROUND OF THE INVENTION

This application is a continuation-in-part of: U.S. Ser. No. 07/797,555, filed Nov. 22, 1991, now abandoned, U.S. Ser. No. 07/838,595, filed Feb. 19, 1992, now abandoned, (which is a continuation-in-part of U.S. Ser. No. 07/817,761, filed Jan. 8, 1992, now abandoned); U.S. Ser. No. 08/063,171, filed May 17, 1993 now abandoned, (which is a continuation-in-part of U.S. Ser. Nos. 07/838,595 and 07/797,555); and U.S. Ser. No. 08/062,946, filed May 17, 1993, now abandoned, (which is a continuation-in-part of U.S. Ser. No. 07/838,595).

The invention relates to porcine interleukin-10 (IL-10) and to the use of, cytokines, e.g., IL-10, to regulate the immune system, e.g., to suppress an unwanted immune response.

IL-10 has been described and cloned in mouse (Fiorentino et al., (1989), *J Exp. Med* 170, 2081–2095; Moore et al., (1990) *Science* 248, 1230–1234), human (Viera et al., (1991) *Proc. Natl. Acad. Sci.* USA 83, 1886–1890) and rat (Feng et al., (1993) *Biochem Biophys Res Commun* 192, 452–8). As with many cytokines, IL-10 appears to have several biological effects and is released by a variety of cells. IL-10 has been reposed to be secreted by monocytes (Fiorentino et al., (1991) *J. Immunol.* 146, 3444: De Waal et al., (1991)*J. Exp. Med.* 174, 1209–1220), B cells (O'Garra et al., (1990) *Int. Immunol.* 2, 821) and the Th1 and Th2 subsets of CD4 cells (Fiorentino et al., (1989), *J Exp. Med* 170, 2081–2095; Del Prete et al., (1993)*J. Immunol.* 150, 353–360).

Th1 cells secrete IL-2, IFN-γ and lymphotoxin (LT). Th2 cells secrete IL-4, IL-5, IL-6 and IL-10 (Fiorentino et al., (1989),*J. Exp. Med* 170, 2081–2095; Viera et al., (1991) *Proc. Natl. Acad Sci.* USA 83, 1886–1890; Cherwinski et al., (1987)*J. Exp. Med.* 166, 1229–1244). The Th1 and Th2 subsets interact: IFN-γ inhibits the proliferation of Th2 cells which respond to either IL-2 or TH-4, but does not inhibit proliferation of Th1 cells (Gajewski, T. & Fitch, F. (1988)*J. Immunol.* 140, 4245–4252; Fernandez-Botran et al., (1988) *J. Exp. Med.* 168, 543-); IL-10, on the other hand, inhibits the synthesis of cytokines by Th1 cells (Fiorentino et al., (1991)*J. Immunol.* 146, 3444; Magilauy et al., (1989)*J. Exp. Med.* 170, 985–990). The Th1 and Th2 subsets are defined in phenotypically, in terms of differential patterns of in vitro cytokine secretion (Mosmann. T & al., e. (1986)*J. Immunol.* 136, 2348–2357; Cherwinski et al., (1987)*J. Exp. Med.* 166, 1229–1244), there is evidence that these patterns occur in vivo as well (Mosmann, T. & Coffman, R. (1989)*Adv. Immunol.* 46, 111–147; Yamamura et al., (1991)*Science* 254, 277; Heinzel et al., (1991)*Proc. Natl. Acad Sci.* USA. 88, 7011; Chatelain et al., (1992)*J. Immunol.* 148, 1182; Papp et al., (1992)*J. Immunol.* 148, 1308).

SUMMARY OF THE INVENTION

In general, the invention features, a purified DNA which includes (or consists essentially of) a DNA sequence encoding a peptide having porcine IL-10 activity. In preferred embodiments: the DNA sequence is at least 85%, more preferably at least 90%, yet more preferably at least 95%, and most preferably at least 98 or 99% homologous with DNA from SEQ ID NO:1; the amino acid sequence of the peptide having IL-10 activity is such that it can be encoded by a nucleic acid which hybridizes under high or low stringency conditions to a nucleic acid which encodes a peptide with the same, or essentially the same, amino acid sequence as the peptide of SEQ ID NO:1; the peptide having IL-10 activity is at least 30, more preferably at least 40, more preferably at least 50, and most preferably at least 60, 80, 100, or 120 amino acid residues in length; the peptide having IL-10 activity is at least 80%, more preferably at least 85%, yet more preferably at least 90%, yet more preferably at least 95%, and a most preferably at least 98 or 99% homologous with an amino acid sequence which is the same, or essentially the same, as the peptide sequence of SEQ ID NO:1; and, the amino acid sequence of the peptide having IL-10 activity is essentially the same as the peptide sequence, or a fragment of the sequence, described in SEQ ID NO:1. In other preferred embodiments the peptide does not contain the residues corresponding to one or more of residues 20–23 of human IL-10, i.e., as compared with human IL-10, the peptide of the embodiment carries a deletion for one or more of the residues 20–23 of human IL-10.

In another aspect, the invention features, a purified DNA which includes (or consists essentially of) a DNA sequence which hybridizes under high or low stringency to a nucleic acid which encodes a peptide with the same, or essentially the same, amino acid sequence as the peptide of SEQ ID NO:1. In preferred embodiments: the DNA sequence is at least 85%, more preferably at least 90%, yet more preferably at least 95%, and most preferably at least 98 or 99% homologous with DNA from of SEQ ID NO:1; the purified DNA encodes a peptide at least 30, more preferably at least 40, more preferably at least 50, and most preferably at least 60, 80, 100, or 120 amino acid residues in length; the purified DNA encodes a peptide at least 80, more preferably at least 85, yet more preferably at least 90, yet more preferably at least 95, and most preferably at least 98 or 99% homologous with an amino acid sequence which is the same, or essentially the same, as the amino acid sequence of SEQ ID NO:1; and, the purified DNA encodes a peptide having essentially the same amino acid sequence, or a fragment of the amino acid sequence, described in SEQ ID NO:1. In other preferred embodiments the peptide does not contain the residues corresponding to one or more of residues 20–23 of human IL-10, i.e., as compared with human IL-10, the peptide of the embodiment carries a deletion for one or more of the residues 20–23 of human IL-10.

In another aspect, the invention features, a purified DNA which includes (or consists essentially of) a sequence encoding a peptide of 20 or more amino acids in length, the peptide having at least 90% homology with an amino acid sequence which is the same, or essentially the same, as the amino acid sequence of SEQ ID NO:1. In preferred embodiments the purified DNA encodes: a peptide which is at least 30, more preferably at least 40, more preferably at least 50, and most preferably at least 60, amino acid residues in length; a peptide which is at least 80, more preferably at least 85, yet more preferably at least 90, yet more preferably at least 95, and most preferably at least 98 or 99% homologous with an amino acid sequence which is the same, or essentially the same, as the amino acid sequence of SEQ ID NO:1; and, a peptide with IL-10 activity. In other preferred embodiments the peptide does not contain the residues corresponding to one or more of residues 20–23 of human IL-10, i.e., as compared with human IL-10, the peptide of the embodiment carries a deletion for one or more of the residues 20–23 of human IL-10.

In another aspect, the invention includes a vector which includes DNA of the invention, preferably a purified DNA of the invention, which encodes a peptide of the invention, e.g.: DNA which includes a sequence encoding a peptide having porcine IL-10 activity; DNA which hybridizes under high or low stringency conditions to a nucleic acid which encodes a peptide with the same, or essentially the same, amino acid sequence of SEQ ID NO:1; DNA which encodes a peptide of essentially the sequence described in SEQ ID NO:1; DNA which includes a sequence encoding a peptide of at least 20, preferably at least 30, more preferably at least 40, more preferably at least 50, and most preferably at least 60, amino acid residues in length; and DNA which encodes a peptide at least 80, more preferably at least 85, yet more preferably at least 90, yet more preferably at least 95, and most preferably at least 98 or 99% homologous with an amino acid sequence which is the same, or essentially the same, as the amino acid sequence of SEQ ID NO:1. Other preferred embodiments include those in which: the DNA sequence is at least 85%, more preferably at least 90%, yet more preferably at least 95%, and most preferably at least 98 or 99% homologous with the DNA sequence of SEQ ID NO:1. In other preferred embodiments the peptide does not contain the residues corresponding to one or more of residues 20–23 of human IL-10, i.e., as compared with human IL-10, the peptide of the embodiment carries a deletion for one or more of the residues 20–23 of human IL-10.

The invention also includes: a cell containing a DNA, preferably a purified DNA, of the invention, preferably, a cell which is capable of expressing a peptide of the invention; an essentially homogeneous population of cells, each of which includes a DNA, preferably a purified DNA, of the invention, and a method for manufacture of a peptide of the invention including culturing a cell which includes a DNA, preferably a purified DNA of the invention in a medium to express the peptide.

In another aspect, the invention features a peptide of the invention, preferably a purified peptide of the invention, e.g.: a peptide having porcine IL-10 activity; a peptide encoded by a DNA which hybridizes under high or low stringency conditions to a nucleic acid which encodes peptide sequence which is the same, or essentially the same, as the amino acid sequence of SEQ ID NO:1; a peptide of essentially the sequence described in SEQ ID NO:1; a peptide of at least 20, preferably at least 30, more preferably at least 40, more preferably at least 50, and most preferably at least 60, amino acid residues in length; and, a peptide having at least 80, more preferably 85, yet more preferably 90, yet more preferably 95, and most preferably at least 98 or 99% homology with an amino acid sequence which is the same, or essentially the same, as the amino acid sequence of SEQ ID NO:1. In other preferred embodiments the peptide does not contain the residues corresponding to one or more of residues 20–23 of human IL-10, i.e., as compared with human IL-10, the peptide of the embodiment carries a deletion for one or more of the residues 20–23 of human IL-10.

In another aspect, the invention features a peptide of the invention, preferably a purified peptide of the invention, produced by expression of a DNA of the invention, preferably a purified DNA of the invention, e.g.: a peptide produced by the expression of: a purified DNA encoding a peptide having porcine IL-10 activity; a peptide expressed from DNA which hybridizes under high or low stringency conditions to a nucleic acid which encodes a peptide with the same, or essentially the same, amino acid sequence as the peptide of SEQ ID NO:1; a peptide expressed from DNA which encodes a peptide of essentially the sequence described in SEQ ID NO:1; a peptide expressed from a purified DNA which includes a sequence encoding a peptide of at least 20, preferably at least 30, more preferably at least 40, more preferably at least 50, and most preferably at least 60, amino acid residues in length; and a peptide expressed from DNA having at least 80, more preferably 85, yet more preferably 90, yet more preferably 95, and most preferably at least 98 or 99% homology with an amino acid sequence which is the same, or essentially the same, as the sequence of SEQ ID NO:1. In other preferred embodiments the peptide does not contain the residues corresponding to one or more of residues 20–23 of human IL-10, i.e., as compared with human IL-10, the peptide of the embodiment carries a deletion for one or more of the residues 20–23 of human IL-10.

In another aspect, the invention features: a therapeutic composition which includes a peptide of the invention and a pharmaceutically acceptable carrier; and, a therapeutic composition which includes a purified DNA of the invention and a pharmaceutically acceptable carrier.

In another aspect, the invention features a transgenic animal, e.g., a transgenic mammal, e.g., a mouse, having a transgene which includes an porcine IL-10 encoding DNA. In preferred embodiments the porcine IL-10 gene or DNA includes a deletion or is mis-expressed.

In general, the invention features, a method of inducing immunological tolerance in a recipient mammal, preferably a mammal which exhibits endothelial MHC class II expression, e.g., a miniature swine, or a primate, e.g., a human, to a graft obtained from a donor mammal of a second, preferably discordant, species. Preferably, the donor is a mammal which exhibits endothelial MHC class II expression, e.g., a non-human primate or a miniature swine. The method includes either or both: increasing the level of the activity of a cytokine which directly, or indirectly (e.g., by the stimulation or inhibition of the level of activity of a second cytokine) promotes tolerance to a graft, e.g., IL-10, IL-4, or TGF-β; or, decreasing the level of the activity of a cytokine which promotes rejection of a graft, i.e., a cytokine which is antagonistic to or inhibits tolerance, e.g., IFNβ, IL-1, IL-2, or IL-12.

In preferred embodiments: the level of a cytokine's activity can be manipulated before the graft is removed from the donor, after the graft is removed from the donor but before the graft is implanted in the recipient, at the time the graft in implanted in the recipient, or after the graft in implanted in the recipient; the level of a cytokine's activity can be manipulated by administering a treatment to the donor, the tissue or organ which will become the graft, the graft or the recipient. For example, a cytokine can be administered prior to, at the time of, or after transplantation of the graft.

The level of a cytokine's activity can be increased or decreased in a number of ways. For example, the level can be increased by: administering, (e.g., intraperitoneally or intravenously to the donor or the recipient, or by direct delivery, e.g., by injection, into the tissue or organ which will serve as the graft, or the graft); an effective amount of the cytokine; an effective amount of a second cytokine which increases the level of activity of the cytokine, e.g., an effective amount of IL-4 (which increases the level of IL-10 activity); or, an effective amount of an inhibitor of a second cytokine which inhibits the level of activity of the cytokine. The level of a cytokine's activity can also be increased by: inducing, in the donor, in the recipient, in the donor tissue which will become the graft, or in the graft, the activity of a subset of T cells, e.g., the Th2 subset, which increases the level of activity of the cytokine, e.g., by promoting the secretion of the cytokine, or inhibiting the activity of a subset of cells, e.g., the Th1 subset, which decreases the level of activity of the cytokine. The level of a cytokine's activity can be decreased by: the administration of an antibody directed against the cytokine; by the administration of an inhibitor, e.g., a competitive inhibitor, of the cytokine; by the administration of a second cytokine which decreases the level of the cytokine's activity, e.g., by decreasing the level of the secretion of the cytokine; or, by inhibiting the activity of a subset of T cells which promote the activity of the cytokine e.g., by administration of an antibody directed against a cell which promotes the cytokine's production, or by the stimulation of the activity of a subset of cells, e.g., the Th2 subset, which decreases the cytokine's level of activity.

Preferred embodiments include those in which: the level of a cytokine is modulated by: the use of a cell which has been engineered to express a product, e.g., a cytokine, which will increase the level of a tolerance-promoting cytokine, or decrease the level of a tolerance-inhibiting cytokine, e.g., by implanting in the graft or the recipient, a cell which expresses a tolerance-promoting cytokine, e.g., IL-10.

A cytokine administered to promote tolerance can be derived from the donor species or from the recipient species but is preferably from the recipient species.

In another aspect, the invention features, a method of inhibiting graft-versus-host-disease (GVHD) in a mammal, preferably a mammal which exhibits endothelial MHC class II expression, e.g., a miniature swine, or a primate, e.g., a human, which is the recipient of a graft obtained from a donor mammal of a second, preferably discordant, species. Preferably, the donor is a mammal which exhibits endothelial MHC class II expression, e.g., a non-human primate or a miniature swine. The method includes either or both: increasing the level of the activity of a cytokine which directly, or indirectly (e.g., by the stimulation or inhibition of the level of activity of a second cytokine) inhibits an immune response mounted by donor cells against the recipient, e.g., IL-10, IL-4, or TGF-β; or, decreasing the level of the activity of a cytokine which promotes an immune response by donor cells against the recipient, i.e., IFN-γ, IL-1, IL-2, or IL-12.

In preferred embodiments: the level of a cytokine's activity can be manipulated before the graft is removed from the donor, after the graft is removed from the donor but before the graft is implanted in the recipient, at the time the graft is implanted in the recipient, or after the graft in implanted in the recipient; the level of a cytokine's activity can be manipulated by administering a treatment to the donor, the tissue or organ which will become the graft, the graft, or the recipient. For example, a cytokine can be administered prior to, at the time of, or after transplantation of the graft.

The level of a cytokine's activity can be increased or decreased in a number of ways. For example, the level can be increased by administering, (e.g., intraperitoneally or intravenously to the donor or the recipient, or by direct delivery, e.g., by injection, into the tissue or organ which will serve as the graft, or the graft): an effective amount of the cytokine; an effective amount of a second cytokine which increases the level of activity of the cytokine, e.g., an effective amount of IL-4, (which increases the level of IL-10 activity); or, an effective amount of an inhibitor of a second cytokine which inhibits the level of activity of the cytokine. The level of a cytokine's activity can also be increased by: inducing, in the donor, in the recipient, in the donor tissue which will become the graft, or in the graft, the activity of a subset of T cells. e.g., the Th2 subset, which increases the level of activity of the cytokine, e.g., by promoting the secretion of the cytokine, or inhibiting the activity of a subset of cells, e.g., the Th1 subset, which decreases the level of activity of the cytokine. The level of a cytokine's activity can be decreased by: the administration of an antibody directed against the cytokine; by the administration of an inhibitor, e.g., a competitive inhibitor, of the cytokine; by the administration of a second cytokine which decreases the level of the cytokine's activity, e.g., by decreasing the level of the secretion of the cytokine; or, by inhibiting the activity of a subset of T cells which promote the activity of the cytokine e.g., by administration of an antibody directed against a cell which promotes the cytokine's production, or by the stimulation of the activity of a subset of cells. e.g., the Th2 subset, which decreases the cytokine's level of activity.

Preferred embodiments include those in which: the level of a cytokine is be modulated by: using a cell which has been engineered to express a product, e.g., a cytokine, which will decrease the level of activity of a cytokine which promotes a donor cell response directed against the host, or decrease the level of such a cytokine, e.g., by implanting in the graft or the recipient, a cell which expresses a cytokine, e.g., IL-10.

A cytokine administered to promote tolerance can be derived from the donor species or from the recipient species but is preferably from the donor species.

In general, the invention features, a method of inducing immunological tolerance in a recipient mammal, preferably a mammal which exhibits endothelial MHC class II expression, e.g., a miniature swine, or a primate, e.g., a human, to a graft obtained from a donor mammal of the same species. The method includes either or both: increasing the level of the activity of a cytokine which directly, or indirectly (e.g., by the stimulation or inhibition of the level of activity of a second cytokine) promotes tolerance to a grail, e.g., IL-10, IL-4, or TGF-β; or, decreasing the level of the activity of a cytokine which promotes rejection of a grail, i.e., a cytokine which is antagonistic to or inhibits tolerance, e.g., IFN-β, IL-1, IL-2, or IL-12.

In preferred embodiments: the level of a cytokine's activity can be manipulated before the graft is removed from the donor, after the graft is removed from the donor but before the graft is implanted in the recipient, at the time the grail is implanted in the recipient, or after the graft is implanted in the recipient; the level of a cytokine's activity can be manipulated by administering a treatment to the donor, the tissue or organ which will become the graft, the graft, or the recipient. For example, a cytokine can be administered prior to, at the time of, or after transplantation of the graft.

The level of a cytokine's activity can be increased or decreased in a number of ways. For example, the level can be increased by administering, (e.g., intraperitoneally or intravenously to the donor or the recipient, or by direct delivery, e.g., by injection, into the tissue or organ which will serve as the graft, or the graft): an effective amount of the cytokine; an effective amount of a second cytokine which increases the level of activity of the cytokine, e.g., an effective amount of IL-4 (which increases the level of IL-10 activity), or an effective amount of an inhibitor of a second cytokine which inhibits the level of activity of the cytokine. The level of a cytokine's activity can also be increased by: inducing, in the donor, recipient, the donor tissue which will become the graft, or the graft, the activity of a subset of T cells, e.g., the Th2 subset, which increases the level of activity of the cytokine, e.g., by promoting the secretion of the cytokine, or inhibiting the activity of a subset of cells, e.g., the Th1 subset, which decreases the level of activity of the cytokine. The level of a cytokine's activity can be decreased by: the administration of an antibody directed against the cytokine; by the administration of an inhibitor, e.g., a competitive inhibitor, of the cytokine; by the administration of a second cytokine which decreases the level of the cytokine's activity, e.g., by decreasing the level of the secretion of the cytokine; or, by inhibiting the activity of a subset of T cells which promote the activity of the cytokine e.g., by administration of an antibody directed against a cell which promotes the cytokine's production, or by the stimulation of the activity of a subset of cells, e.g., the Th2 subset, which decreases the cytokine's level of activity.

Preferred embodiments include those in which: the level of a cytokine is be modulated by: using a cell which has been engineered to express a product, e.g., a cytokine, which will increase the level of a tolerance-promoting cytokine, or decrease the level of a tolerance-inhibiting cytokine, e.g., by implanting in the graft or the recipient, a cell which expresses a tolerance-promoting cytokine, e.g., IL-10.

In another aspect, the invention features, a method of inhibiting graft-versus-host-disease (GVHD) in a mammal, preferably a mammal which exhibits endothelial MHC class II expression, e.g., a miniature swine, or a primate, e.g., a human, which is the recipient of a graft obtained from a donor mammal of the same species. Preferably, the donor is a mammal which exhibits endothelial MHC class II expression, e.g., a non-human primate or a miniature swine. The method includes either or both: increasing the level of the activity of a cytokine which directly, or indirectly (e.g., by the stimulation or inhibition of the level of activity of a second cytokine) inhibits an immune response mounted by donor cells against the recipient, e.g., IL-10, IL-4, or TGF-β; or, decreasing the level of the activity of a cytokine which promotes an immune response by donor cells against the recipient, i.e., IFN-γ, IL-1, IL-2, or IL-12.

In preferred embodiments: the level of a cytokine's activity can be manipulated before the graft is removed from the donor, after the graft is removed from the donor but before the graft is implanted in the recipient, at the time the graft is implanted in the recipient, or after the graft is implanted in the recipient; the level of a cytokine's activity can be manipulated by administering a treatment to the donor, the tissue or organ which will become the graft, the graft, or the recipient. For example, a cytokine can be administered prior to, at the time of, or after transplantation of the graft.

The level of a cytokine's activity can be increased or decreased in a number of ways. For example, the level can be increased by administering, (e.g., intraperitoneally or intravenously to the donor or the recipient, or by direct delivery, e.g., by injection, into the tissue or organ which will serve as the graft, or the graft): an effective amount of the cytokine; an effective amount of a second cytokine which increases the level of activity of the cytokine, e.g., an effective amount of IL-4 (which increases the level of IL-10 activity); or an effective amount of an inhibitor of a second cytokine which inhibits the level of activity of the cytokine. The level of a cytokine's activity can also be increased by inducing, in the donor, in the recipient, in the donor tissue which will become the graft, or in the graft, the activity of a subset of T cells, e.g., the Th2 subset, which increases the level of activity of the cytokine, e.g., by promoting the secretion of the cytokine, or inhibiting the activity of a subset of cells, e.g., the Th1 subset, which decreases the level of activity of the cytokine. The level of a cytokine's activity can be decreased by: the administration of an antibody directed against the cytokine; by the administration of an inhibitor, e.g., a competitive inhibitor, of the cytokine; by the administration of a second cytokine which decreases the level of the cytokine's activity, e.g., by decreasing the level of the secretion of the cytokine; or, by inhibiting the activity of a subset of T cells which promote the activity of the cytokine e.g., by administration of an antibody directed against a cell which promotes the cytokine's production, or by the stimulation of the activity of a subset of cells, e.g., the Th2 subset, which decreases the cytokine's level of activity.

Preferred embodiments include those in which: the level of a cytokine is be modulated by: using a cell which has been engineered to express a product, e.g., a cytokine, which will decrease the level of activity of a cytokine which promotes a donor cell response directed against the host, or decrease the level of such a cytokine, e.g., by implanting in the graft or the recipient, a cell which expresses a cytokine, e.g., IL-10.

The invention also includes other methods of inducing tolerance. These methods (which are described below) can be used alone or in combination with the above-described methods of promoting tolerance or inhibiting GVHD. For example, one or more of: the short-term administration of a help reducing agent, e.g., a short high dose course of cyclosporine A (CsA) treatment to induce tolerance to an antigen e.g., and unmatched donor Class I or other minor unmatched donor antigens (the use of short-term help reduction is described in U.S. Ser. No. 08/063, 171, filed May 17, 1993, hereby incorporated by reference); the implantation of transduced bone marrow cells to induce tolerance to an antigen, e.g., an antigen on an unmatched donor Class II graft (the use of transduced cells to induce tolerance is described in U.S. Ser. No. 07/797,555, filed on Nov. 22, 1991, hereby incorporated by reference); the implantation of donor bone marrow cells to induce tolerance to an antigen, e.g., an antigen on an unmatched donor Class II grafts (the use of donor species bone marrow cells to induce tolerance is described in U.S. Ser. No. 07/838,595, filed Feb. 19, 1992, hereby incorporated by reference); or the use of xenogeneic thymic graft to induce tolerance (the use of thymic xenograft to induce tolerance is described in U.S. Ser. No. 08/062,946, filed on May 17, 1993, hereby incorporated by reference); can be used alone, in combination with one another, or in combination with methods of increasing the level of the activity of a tolerance promoting or GVHD inhibiting cytokine or decreasing the level of activity of an a tolerance inhibiting or GVHD promoting cytokine described above.

Accordingly, in another aspect, the invention features, a method of inducing tolerance in a recipient primate, e.g., a human, to an allograft from a donor primate including administering to the recipient a short course of help reducing treatment, e.g., a short course of high dose cyclosporine, and preferably, administering a treatment which increases the level of the activity of a tolerance promoting or GVHD inhibiting cytokine or decreases the level of activity of an a tolerance inhibiting or GVHD promoting cytokine.

In preferred embodiments the duration of the short course of help reducing treatment is approximately equal to or is less than the period required for mature T cells of the recipient species to initiate rejection of an antigen after first being stimulated by the antigen (in humans this is usually 8–12 days, preferably about 10 days); in more preferred embodiments the duration is approximately equal to or is less than two, three, four, five, or ten times the period required for mature T cells of the recipient to initiate rejection of an antigen after first being stimulated by the antigen.

In other preferred embodiments, the short course of help reducing treatment is administered in the absence of a treatment which may stimulate the release of a cytokine by mature T cells in the recipient, e.g., in the absence of Prednisone (17,21-dihydroxypregna-1,4-diene-3,11,20-trione).

In preferred embodiments: the help reducing treatment is begun before or at about the time the graft is introduced; the short course is preoperative, the short course is postoperative; the donor and recipient are Class I matched.

In another aspect, the invention features a method of inducing tolerance in a recipient mammal, e.g., a primate, e.g., a human, of a first species, to graft from a mammal, e.g., a swine, e.g., a miniature swine, of a second species, which graft expresses a major histocompatibility complex (MHC) antigen. The method includes: inserting DNA encoding an MHC antigen of the second species into a bone marrow hematopoietic stem cell of the recipient mammal; allowing the MHC antigen encoding DNA to be expressed in the recipient; preferably, administering to the recipient a short course of help receding treatment, e.g., a short course of high dose cyclosporine treatment; and preferably, administering a treatment which increases the level of the activity of a tolerance promoting or GVHD inhibiting cytokine or decreases the level of activity of an a tolerance inhibiting or GVHD promoting cytokine.

Preferred embodiments include those in which: the cell is removed from the recipient mammal prior to the DNA insertion and returned to the recipient mammal after the DNA insertion; the DNA is obtained from the individual mammal from which the graft is obtained; the DNA is obtained from an individual mammal which is syngeneic with the individual mammal from which the graft is obtained; the DNA is obtained from an individual mammal which is MHC matched, and preferably identical, with the individual mammal from which the graft is obtained; the DNA includes an MHC Class 1 gene; the DNA includes an MHC Class II gene; the DNA is inserted into the cell by transduction, e.g., by a retrovirus, e.g., by a Moloney-based retrovirus; and the DNA is expressed in bone marrow cells and/or peripheral blood cells of the recipient for at least 14, preferably 30, more preferably 60, and most preferably 120 days, after the DNA is introduced into the recipient.

In another aspect, the invention features a method of inducing tolerance in a recipient mammal, preferably a primate, e.g., a human, to a graft obtained from a donor of the same species, which graft expresses an MHC antigen. The method includes inserting DNA encoding an MHC antigen of the donor into a bone marrow hematopoietic stem cell of the recipient; allowing the MHC antigen encoding DNA to be expressed in the recipient; preferably, administering to the recipient a short course of help reducing treatment, e.g., a short course of high dose cyclosporine; and, preferably, administering a treatment which increases the level of the activity of a tolerance promoting or GVHD inhibiting cytokine or decreases the level of activity of an a tolerance inhibiting or GVHD promoting cytokine.

Preferred embodiments include those in which: the cell is removed from the recipient prior to the DNA insertion and returned to the recipient after the DNA insertion; the DNA includes a MHC Class I gene; the DNA includes a MHC Class II gene; the DNA is inserted into the cell by transduction, e.g., by a retrovirus, e.g., by a Moloney-based retrovirus; and the DNA is expressed in bone marrow cells and/or peripheral blood cells of the recipient at least 14, preferably 30, more preferably 60, and most preferably 120 days, after the DNA is introduced into the recipient.

In another aspect, the invention features a method of inducing tolerance in a recipient mammal of a first species, e.g., a primate, e.g., a human, to a graft obtained from a mammal of a second, preferably discordant species, e.g., a swine, e.g., a miniature swine, or a discordant primate species. The method includes: prior to or simultaneous with transplantation of the graft, introducing, e.g., by intravenous injection, into the recipient mammal hematopoietic stem cells, e.g., bone marrow cells or fetal or neonatal liver or spleen cells, of the second species (preferably the hematopoietic stem cells home to a site in the recipient mammal); inactivating the natural killer cells of said recipient mammal, e.g., by prior to introducing the hematopoietic stem cells into the recipient mammal, introducing into the recipient mammal an anti-body capable of binding to natural killer cells of a said recipient mammal; preferably, administering to the recipient a short course of help reducing treatment, e.g., a short course of high dose cyclosporine, and, preferably, administering a treatment which increases the level of the activity of a tolerance promoting or GVHD inhibiting cytokine or decreases the level of activity of an a tolerance inhibiting or GVHD promoting cytokine.

The hematopoietic cells prepare the recipient for the graft that follows, by inducing tolerance at both the B-cell and T-cell levels. Preferably, hematopoietic cells are fetal or neonatal liver or spleen, or bone marrow cells, including immature cells (i.e., undifferentiated hematopoietic stem cells; these desired cells can be separated out of the bone marrow prior to administration), or a complex bone marrow sample including such cells can be used.

One source of anti-NK antibody is anti-human thymocyte polyclonal anti-serum. Preferably, a second, anti-mature T cell antibody can be administered as well, which lyses T cells as well as NK cells. Lysing T cells is advantageous for both bone marrow and xenograft survival. Anti-T cell antibodies are present, along with anti-NK antibodies, in anti-thymocyte anti-serum. Repeated doses of anti-NK or anti-T cell anti-body may be preferable. Monoclonal preparations can be used in the methods of the invention.

Other preferred embodiments include: the step of introducing into the recipient mammal, donor species-specific stromal tissue, preferably hematopoietic stromal tissue, e.g., fetal or neonatal liver or thymus. In preferred embodiments: the stromal tissue is introduced simultaneously with, or prior to, the hematopoietic stem cells; the hematopoietic stem cells are introduced simultaneously with, or prior to, the antibody.

Other preferred embodiments include those in which: the same mammal of the second species is the donor of one or both the graft and the hematopoietic cells; and the antibody is an anti-human thymocyte polyclonal anti-serum, obtained, e.g., from a horse or pig.

Other preferred embodiments include: the step of prior to hematopoietic stem cell transplantation, irradiating the recipient mammal with low dose, e.g., between about 100 and 400 rads, whole body irradiation to deplete or partially deplete the bone marrow of said recipient; and the step of prior to hematopoietic stem cell transplantation, irradiating the recipient mammal with, e.g., about 700 rads of thymic irradiation.

Other preferred embodiments include: the step of prior to hematopoietic stem cell transplantation, depleting natural antibodies from the blood of the recipient mammal, e.g., by hemoperfusing an organ, e.g., a liver or a kidney, obtained from a mammal of the second species. (In organ hemoperfusion antibodies in the blood bind to antigens on the cell surfaces of the organ and are thus removed from the blood.)

In other preferred embodiments: the method further includes, prior to hematopoietic stem cell transplantation, introducing into the recipient an anti-body capable of binding to mature T cells of said recipient mammal. Other preferred embodiments further include the step of introducing into the recipient a graft obtained from the donor, e.g., a graft which is obtained from a different organ than the hematopoietic stem cells, e.g., a liver or a kidney.

In another aspect, the invention features a method of inducing tolerance in a recipient mammal, preferably a primate, e.g., a human, to a graft obtained from a donor, e.g., of the same species. The method includes: prior to or simultaneous with transplantation of the graft, introducing, e.g., by intravenous injection, into the recipient hematopoietic stem cells, e.g. bone marrow cells or fetal or neonatal liver or spleen cells, of a mammal, preferably the donor (preferably the hematopoietic stem cells home to a site in the recipient); inactivating the natural killer cells of the recipient, e.g., by prior to introducing the hematopoietic stem cells into the recipient, introducing into the recipient an anti-body capable of binding to natural killer cells of the recipient; preferably, administering to the recipient a short course of help reducing treatment, e.g., a short course of high dose cyclosporine, and, preferably, administering a treatment which increases the level of the activity of a tolerance promoting or GVHD inhibiting cytokine or decreases the level of activity of an a tolerance inhibiting or GVHD promoting cytokine.

In preferred embodiments the duration of the short course of help reducing treatment is approximately equal to or is less than the period required for mature T cells of the recipient species to initiate rejection of an antigen after first being stimulated by the antigen; in more preferred embodiments the duration is approximately equal to or is less than two, three, four, five, or ten times the period required for a mature T cell of the recipient species to initiate rejection of an antigen after first being stimulated by the antigen.

In other preferred embodiments the short course of help reducing treatment is administered in the absence of a treatment which stimulates the release of a cytokine by mature T cells in the recipient, e.g., in the absence of Prednisone.

In preferred embodiments: the help reducing treatment is begun before or at about the time the graft is introduced; the short course is preoperative, the short course is postoperative; the donor and recipient are Class I matched.

In preferred embodiments the hematopoietic stem cells are introduced simultaneously with, or prior to administration of the antibody; the antibody is an anti-human thymocyte polyclonal anti-serum; and the anti-serum is obtained from a horse or pig.

Other preferred embodiments include: the further step of, prior to hematopoietic stem cell transplantation, introducing into the recipient mammal an antibody capable of binding to mature T cells of the recipient mammal; and those in which the same individual is the donor of both the graft and the bone marrow.

Other preferred embodiments include: further including the step of prior to hematopoietic stem cell transplantation, irradiating the recipient with low dose, e.g., between about 100 and 400 rads, whole body irradiation to completely or partially deplete the bone marrow of the recipient; and further including the step of prior to hematopoietic stem cell transplantation, irradiating the recipient with, e.g., about 700 rads of thymic irradiation. Other preferred embodiments include: the further step prior of to bone marrow transplantation, absorbing natural antibodies from the blood of the recipient by hemoperfusing an organ, e.g., the liver, or a kidney, obtained from the donor.

Preferred embodiments include: the step of introducing into the recipient mammal, donor species-specific stromal tissue, preferably hematopoietic stromal tissue, e.g., fetal liver or thymus.

Other preferred embodiments further include the step of introducing into the recipient, a graft obtained from the donor, e.g., a graft which is obtained from a different organ than the hematopoietic stem cells, e.g., a liver or a kidney.

In another aspect, the invention features, a method of inducing tolerance in a recipient mammal. e.g., a primate, e.g., a human, of a first species, preferably an endothelial MHC expressing species, to a graft obtained from a mammal of a second species, e.g., a discordant species, preferably an endothelial MHC expressing species. The method includes: prior to or simultaneous with transplantation of the graft, introducing into the recipient mammal thymic tissue, e.g., thymic epithelium, preferably fetal thymic tissue, of the second species; preferably, administering a treatment which increases the level of the activity of a tolerance promoting or GVHD inhibiting cytokine or decreases the level of activity of an a tolerance inhibiting or GVHD promoting cytokine; and, implanting the graft is the recipient. The thymic tissue prepares the recipient for the graft that follows, by inducing immunological tolerance at both the B-cell and T-cell levels.

Preferred embodiments include other steps to promote acceptance of the graft thymus and the induction of immunological tolerance or to otherwise optimize the procedure. In preferred embodiments: liver tissue, preferably fetal liver tissue, is implanted with the thymic tissue; donor hemopoietic cells, e.g., fetal liver cells, are administered to the recipient, e.g., a suspension of fetal liver cells administered intraperitoneally; the recipient is thymectomized, preferably before or at the time the xenograft thymic tissue is introduced; the method includes prior to or at the time of introducing the thymic tissue into the recipient mammal, introducing into the recipient mammal an antibody capable of binding to natural killer (NK) cells of the recipient mammal, to prevent NK mediated rejection of the thymic tissue; the method includes prior to or at the time of introducing the thymic tissue into the recipient mammal, introducing into the recipient mammal an antibody capable of binding to T cells of the recipient mammal. An anti-mature T cell antibody which lyses T cells as well as NK cells can be administered. Lysing T cells is advantageous for both thymic tissue and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

Other preferred embodiments include those in which: the recipient does not receive hemopoietic cells from the donor or the donor species: the same mammal of the second species is the donor of both the graft and the thymic tissue; the donor mammal is a swine, e.g., a miniature swine; and anti-human thymocyte polyclonal anti-serum, obtained, e.g., from a horse or pig is administered to the recipient.

Other preferred embodiments include: the step of prior to thymic tissue transplantation, irradiating the recipient mammal with low dose, e.g., between about 100 and 400 rads, whole body irradiation; and the step of prior to hematopoietic stem cell transplantation, irradiating the recipient mammal with, e.g., about 700 rads of thymic irradiation.

Preferred embodiments includes: the step of prior to thymic tissue transplantation, absorbing natural antibodies from the blood of the recipient mammal, e.g., by hemoperfusing an organ, e.g., a liver or a kidney, obtained from a mammal of the second species; those in which the graft is obtained from a different organ than is the thymic tissue.

"Help reduction", as used herein, means the reduction of T cell help by the inhibition of the release of at least one cytokine, e.g., any of IL-2, IL-4, IL-6, gamma interferon, or TNF, from T cells of the recipient at the time of the first exposure to an antigen to which tolerance is desired. The inhibition induced in a recipient's T cell secretion of a cytokine must be sufficient such that the recipient is tolerized to an antigen which is administered during the reduction of help. Although not being bound by theory, it is believed that the level of reduction is one which substantially eliminates the initial burst of IL-2 which accompanies the first recognition of a foreign antigen but which does not eliminate all mature T cells, which cells may be important in educating and producing tolerance.

"A help reducing agent", as used herein, is an agent, e.g., an immunosuppressive drug, which results in the reduction of cytokine release. Examples of help reducing agents are cyclosporine, FK-506, and rapamycin. Anti-T cell antibodies, because they can eliminate T cells, are not preferred for use as help reducing agents. A help reducing agent must be administered in sufficient dose to give the level of inhibition of cytokine release which will result in tolerance. The help reducing agent should be administered in the absence of treatments which promote cytokine, e.g., IL-2, release. Putative agents help reducing agents can be prescreened by in vitro or in vivo tests, e.g., by contacting the putative agent with T cells and determining the ability of the treated T cells to release a cytokine, e.g., IL-2. The inhibition of cytokine release is indicative of the putative agent's efficacy as a help reducing agent. Such prescreened putative agents can then be further tested in a kidney transplant assay. In a kidney transplant assay a putative help reducing agent is tested for efficacy by administering the putative agent to a recipient monkey and then implanting a kidney from a Class II matched Class I and minor antigen mismatched donor monkey into the recipient. Tolerance to the donor kidney (as indicated by prolonged acceptance of the graft) is indicative that the putative agent is, at the dosage tested, a help reducing agent.

"Short course of a help reducing agent", as used herein, means a transitory non-chronic course of treatment. The treatment should begin before or at about the time of transplantation of the graft. Alternatively, the treatment can begin before or at about the time of the recipient's first exposure to donor antigens. Optimally, the treatment lasts for a time which is approximately equal to or less than the period required for mature T cells of the recipient species to initiate rejection of an antigen after first being stimulated by the antigen. The duration of the treatment can be extended to a time approximately equal to or less than two, three, four, five, or ten times, the period required for a mature T cell of the recipient species to initiate rejection of an antigen after first being stimulated by the antigen. The duration will usually be at least equal to the time required for mature T cells of the recipient species to initiate rejection of an antigen after first being stimulated by the antigen. In pigs and monkeys, about 12 days of treatment is sufficient. Experiments with cyclosporine A (10 mg/kg) in pigs show that 6 days is not sufficient. Other experiments in monkeys show that IL-2 administered on day 8, 9, or 10 of cyclosporine A treatment will result in rejection of the transplanted tissue. Thus, 8, 9, or 10 days is probably not sufficient in pigs. In monkeys, a dose of 10 mg/kg cyclosporine with a blood level of about 500–1,000 ng/ml is sufficient to induce tolerance to Class II matched Class I and minor agtigen mismatched kidneys. The same blood level, 500–1,000 ng/ml, is sufficient to induce tolerance in pigs. Long-term administration of 5 mg/kg prevents rejection (by long term immune suppression) but does not result in tolerance.

"Tolerance", as used herein, refers to the inhibition of a graft recipient's immune response which would otherwise occur, e.g., in response to the introduction of a non-self MHC antigen into the recipient. Tolerance can involve humoral, cellular, or both humoral and cellular responses.

"Hematopoietic stem cell", as used herein, refers to a cell, e.g., a bone marrow cell which is capable of developing into a mature myeloid and/or lymphoid cell. For example, stem cells derived from the cord blood of the recipient or the donor can be used in methods of the invention. See U.S. Pat. No. 5,192,553, hereby incorporated by reference, and U.S. Pat. No. 5,004,681, hereby incorporated by reference. "MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes. HLA genes. MHC antigens in swine, e.g., miniature swine, include the products (and fragments and analogs thereof) of the SLA genes, e.g., the DRB gene.

"Miniature swine", as used herein, refers to wholly or partially inbred animals. "Graft", as used herein, refers to a body part, organ, tissue, or cells. Grafts may consist of organs such as liver, kidney, heart or lung; body parts such as bone or skeletal matrix; tissue such as skin, intestines, endocrine glands; or progenitor stem cells of various types.

"A discordant species combination", as used herein, refers to two species in which hyperacute rejection occurs when a graft is grafted from one to the other. Generally, discordant species are from different orders, while non-discordant species are from the same order. For example, rats and mice are non-discordant species, i.e. their MHC antigens are substantially similar, and they are members of the same order, rodentia. "Stromal tissue", as used herein, refers to the supporting tissue or matrix of an organ, as distinguished from its functional elements or parenchyma.

Substantially pure DNA is DNA that is not immediately contiguous with both of the coding sequence with which it is immediately contiguous (i.e., one 5' end and one at the 3' end) in the naturally-occurring genome of the organism from which the DNA is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonulease treatment) independent of other DNA sequences. Substantially pure DNA also includes a recombinant DNA which is part of a hybrid gene encoding additional porcine IL-1- sequence.

Homologous refers to the sequence similarity between two porcine IL-1- molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10, of the positions in two sequences are matched or homologous then the two sequences are 60% homologous. By way of example, the DNA sequences ATTGCC and TATGGC share 50% homology.

A substantially pure preparation of a peptide, e.g., porcine IL-10, is a preparation which is substantially free of the peptides with which it naturally occurs in a cell or with which it naturally occurs when secreted by a cell. A purified preparation can include degradation products produced by proteolytic degradation of the original peptide.

Peptide, as used herein, refers to peptides, proteins, and polypeptides.

A transgene is defined as a piece of DNA which is inserted by artifice into a cell and becomes a part of the genome of an animal which develops in whole or part from that cell. Such a transgene may be partly or entirely heterologous to the transgenic animal.

A peptide has porcine IL-10 biological activity if it has one or more of the following properties: 1. When administered to T cells the peptide inhibits the ability of the T cells to release or produce IL-2;2. When administered to T cells the peptide inhibits the ability of the T cells to release or produce gamma interferon; and, 3. The peptide is capable of competitively inhibiting the binding of IL-10 to cells, e.g., to T cells having IL-10 receptors, preferably the binding of porcine IL-10 to porcine T cells.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms decreased expression (as compared with wild type) in a predetermined cell type or tissue type; a pattern of expression that differs from wild type in terms of the size, amino acid sequence, post-transitional modification, or biological activity of an IL-10; a pattern of expression that differs from wild type in terms of the effect of an environmental stimulus or extra-cellular stimulus on expression of the gene, e.g., a pattern of increased or decreased expression (as compared with wild type) in the presence of an increase or decrease in the strength of the stimulus.

An animal with endothelial MHC class II expression, as used herein, refers to an animal that expresses MHC class II molecules on at least some of its endothelial cells, and preferably on the endothelial cells of a tissue or organ which is used for transplantation.

A transgenic animal, e.g., a transgenic mouse, is an animal having cells that contain a transgene, which transgene was introduced into the animal, or an ancestor of the animal, at a prenatal, e.g., an embryonic, stage.

Porcine IL-10 peptides of the invention can be used e.g., as follows: to study the role of IL-10 in the functioning of the immune system, e.g., to study the interaction of IL-10 with other components of the immune system. e.g., to study the binding of the porcine IL-10 to cells, e.g., to determine whether a cell carries a porcine IL-10 receptor or to determine the number of porcine IL-10 receptors present on a cell; to study the differences and similarities between porcine IL-10 and IL-10's of various species, e.g., to identify conserved and nonconserved regions; to study the interaction of porcine cytokines with components of the immune systems of other species, e.g., humans; to investigate the role of donor cytokines in GVHD in xenografts; and to promote tolerance to a graft and to inhibit donor cell immune responses directed against a graft recipient. Nucleic acids encoding IL-10 can be used to generate IL-10 for use in the studies and methods described above as well as to generate fragments and mutants of IL-10 useful e.g., in studies to define the active site of the molecule or in developing IL-10 agonists or antagonists. Transgenic animals with an IL-10 gene are useful in studying the role of IL-10 in the immune system. The methods of the invention are useful for developing new treatments and for prolonging the acceptance of an allograft or a xenograft and in inhibiting GVHD.

Other features and advantages of the invention will be apparent from the following description and from the claims.

BRIEF DESCRIPTION OF THE DRAWINGS

FIG. 1 is a diagram of the amino acid sequence of a porcine IL-10 and the DNA sequence of a porcine IL-10 cDNA (SEQ ID NO:1).

DETAILED DESCRIPTION

Figure 2:
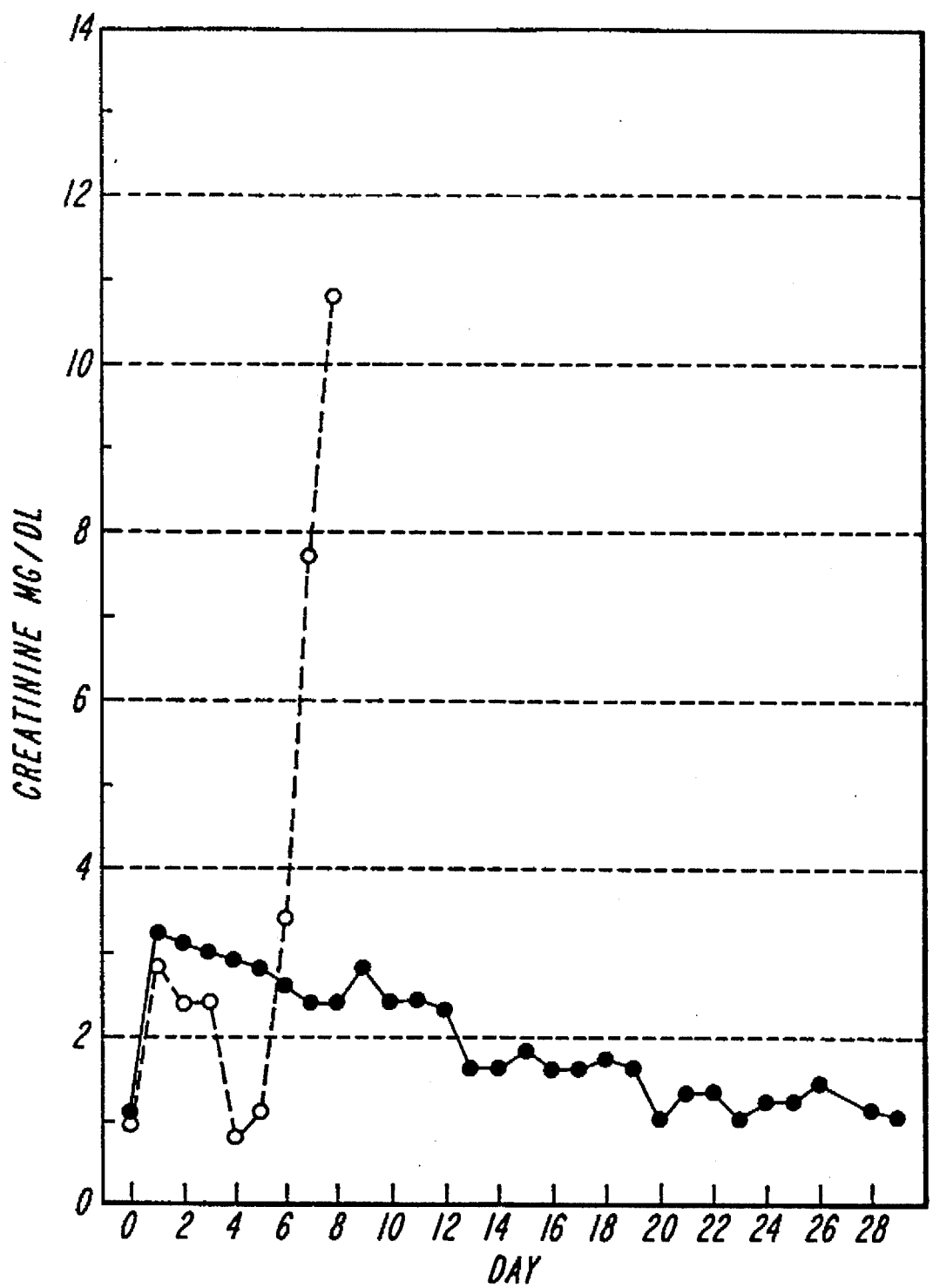
FIG. 2 is a graph of creatine evolution in mg/dl from a tolerant pig (pig#10349), solid circles, and a rejecting pig (pig#10348), open circles.

Generation of a Porcine IL-10 specific probe

A porcine IL-10 probe was made as follows. Polymerase chain reaction (PCR) was performed on cDNA made from RNA extracted from porcine peripheral blood leukocytes using primers which corresponded to regions of maximal similarity between mouse and human IL-10 sequences. TTAAGGGTTACTTGGGTT (SEQ ID NO:2) was used as a 5' (sense) primer and TTA(CGT)CA(T)C(T)TTA(G)TTC(T-)TCA(G)CAA(CGT)G (SEQ ID NO:3) was used as a 3' (antisense) primer. The letters in parentheses indicates degeneracy at the previous position.

PCR with these primers allowed amplification of a fragment 183 base pairs in length. The fragment was sequenced and found to share 86% homology with the corresponding sequence of human IL-10. The sequence of the 183 bp probe corresponded to base pairs 257–440 of human IL-10 and base pairs 287–470 of the pig sequence. This fragment was subcloned in pBst and used as probe to screen a porcine cDNA library, as described below.

Cloning of porcine IL-10

The pig specific IL-10 fragment described above was used to as probe a cDNA library made from PHA activated pig splenocytes. Plating and screening of over 600,000 phages resulted in two plaques which were strongly positive after overnight exposure. The two positive clones were picked and replated. At the third plating all plaques were positive for one of the two original clones. After excision of the plasmid by a helper phage (Exassist. Stratagene), a large amount of plasmid DNA was prepared by maxiprep and the plasmid DNA digested with EcoR I and Xho I (these restriction enzymes recognize the cloning sites of the library). The insert DNA was about 1.3 kb in size, which corresponds well with RNA transcript size observed in Northern blot experiments.

The library was constructed and screened as follows. Poly(A)+RNA was extracted from PHA activated splenocytes, the presence of IL-10 transcripts in the poly (A)+RNA confirmed by northern blot, cDNA made from the poly(A)+RNA, and the cDNA inserted into Lambda Zap to yield a porcine cDNA library. Pig IL-10 cDNA clones were detected by colony hybridization with the pig IL-10 specific probe described above.

Sequence analysis of porcine IL-10

Figure 1:
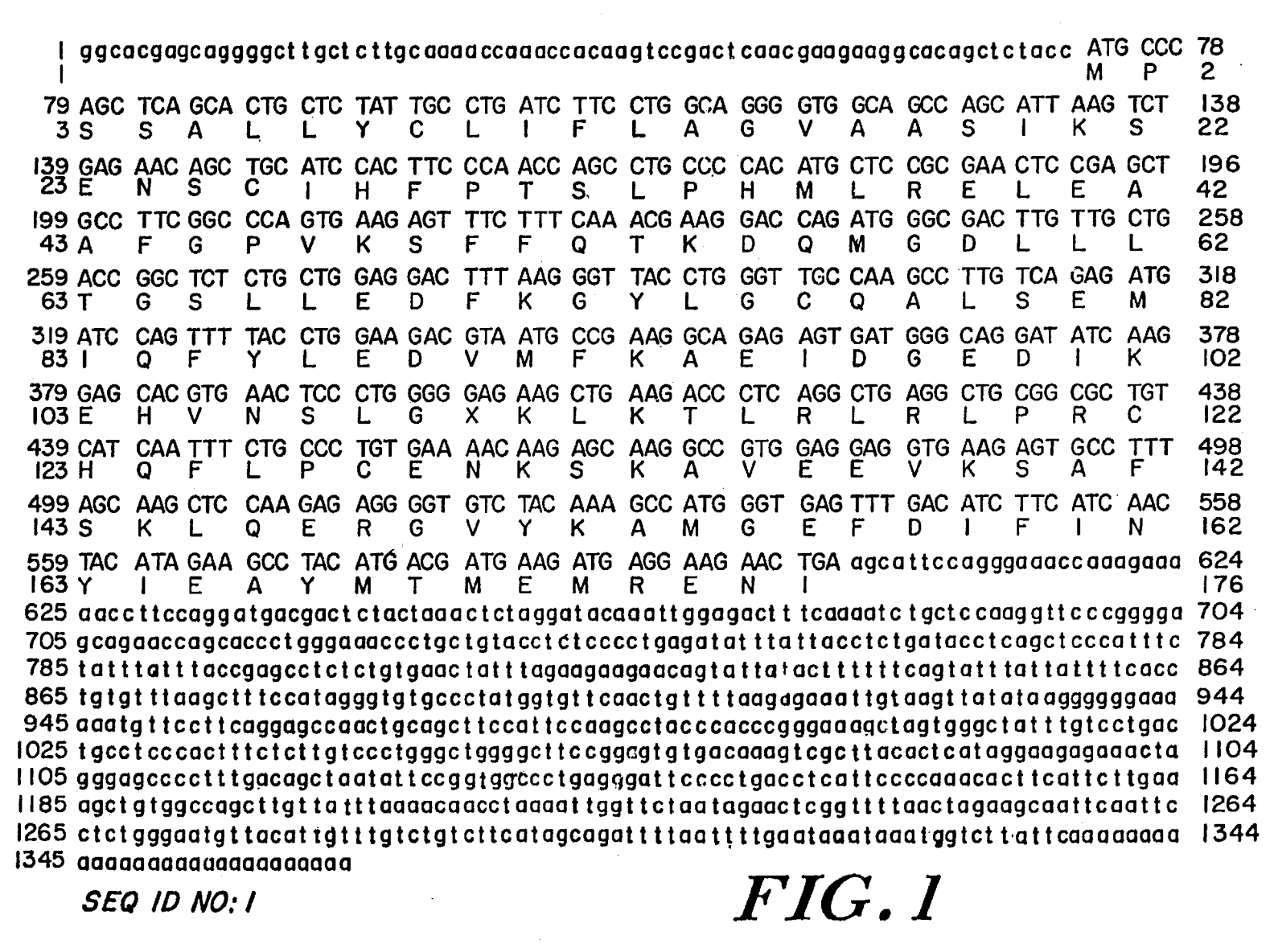

The sequence of porcine IL-10 is shown in FIG. 1. SEQ ID NO:1 The full length cDNA is 1336 base pairs in length (exclusive of the polyA tail). The DNA sequence contains an open reaching frame (ORF) encoding a protein of 175 amino acids. At the nucleotide level, porcine IL-10 is 82% homologous with the human IL-10 sequence and 75% homologous with the mouse IL-10 sequence. At the amino acid level the porcine peptide is 74% homologous with human and 68% homologous with the mouse sequence. Porcine IL-10 differs from human IL-10 in a number of other ways. The pig sequence shows a gap of four amino acids in position 20 to 23, as compared with the human and mouse sequences. The pig protein has an additional amino acid at the end of the protein and is 3 amino acids shorter than the human and mouse proteins, which are 178 amino acids long. (The deletion at 20 to 23 was shown not due to an artifact of cloning by sequencing this specific region of IL-10 on 3 different pig samples. RNA preparations previously shown by northern blot to contain IL-10 transcripts were subjected to reverse transcriptase PCR using primers bounding the region, and the resulting DNA's sequenced.) The pig protein contains one potential N-linked glycosylation site at Asn 130, 5 cysteine residues, and 9 methionines. The calculated molecular weight of the porcine protein is 19,921 daltons.

DNA sequence analysis was performed on DNA excised from lamda Zap (Stratagene) using the Bluescript SK vector, and the sequence 2.0 kit (United States Biochemical). Both strands of the DNA were sequenced. M13 and M13 reverse primers and a set of 8 different internal primers derived from previously determined sequences were used in the sequencing.

Transfection of COS cells and expression of recombinant IL-10

IL-10 cDNA was cleaved with EcoR1/Rsal to remove the untranslated 3 region. The resulting 780 bp fragment containing the ORF was subcloned in an expression vector (pcDNA1) and transfected into COS cells. Translations resulted in two bands under reducing conditions, one at about 19–20 kd, which corresponds well with the expected size, and one at about 16–17 kd.

These experiments were performed as follows: 1×10⁶ COSM-6 cells, plated in DMEM (GIBCO) containing 10% Nuserum (Collaborative Biomedicals, Bedford, Mass.) in a 10 cm dish, were transfected with 10 µg of plasmid SP 161.5 (the EcoRI×Rsal fragment from pSW 10 cloned into EcoRI× EcoRV pcDNA1.Amp) using DEAE-dextran (Sigma).

Forty-two hours later, the transfected cells were labeled with 0.125 mCi/ml[$^{35}$S]-methionine (Dupont-NEN) by the protocol for short-term labeling of adherent cells in Current Protocols in Molecular Biology Section 10.18.3. After 3.5 hours, the supernatant was removed from the cells. Ten and 30 µl samples of the supernatants, reduced and nonreduced, were loaded onto a 15% SDS-PAGE gel that was run at 4 mAmps overnight (protocol from Current Protocols in Molecular Biology Section 10.2.4), soaked in EnHance (Dupont-NEN), dried down onto Whatmann 3 mm paper, and exposed to film.

IL-10 expression and tolerance

The role of IL-10 in the acceptance or rejection of class II matched class I mismatched organ transplants was studied in partially inbred miniature swine (NIH minipigs). The genetic characteristics of the inbred minipig herd have been described, see, e.g., (Pescovitz et al., (1983) *Translplant Proc.* 15, 1124; Pescovitz et al., (1984) *J. Exp. Med.* 160, 1495). An intra-MHC recombinant haplotype g (class I$^{cc}$ class II$^{dd}$) allows transplants to be performed across isolated class I disparities. Without immune suppression (or other tolerance including treatment) class I disparate renal allografts are rejected within 8 to 11 days. Long term tolerance to class I-disparate renal allografts can be induced by a short course of post-transplant Cyclosporine A (CyA) (10 mg/kg/day for 12 days) (Rosengard et al., (1992) *Transplantation* 54, 490–497). The existence of a model in which tolerance and rejection can be reliably and repeatably reproduced allows the investigation of the role of cytokines in the induction of tolerance.

The typical evolution of a rejecting animal and a tolerant animal is shown in FIG. 2. Both animals were the recipient of a class I mismatched kidney graft. The tolerant animal received 10 mg/kg/day of CyA for 12 days after the transplant. The tolerant animal exhibited a post-transplant acute tubular necrosis and recovered normal renal function in about 12 days.

Figure 3:
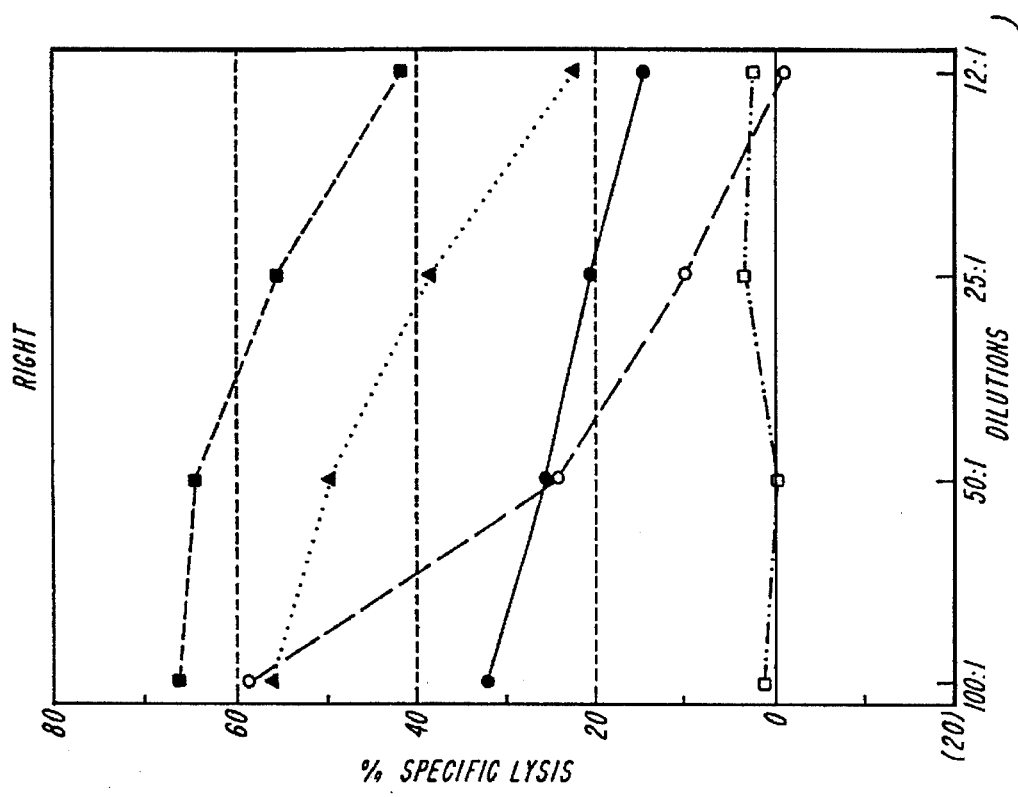
FIG. 3 is a depiction of cytotoxic reactivity of a tolerant (left) and rejecter (right) animal. The genotypes in the left panel (tolerant animal) are as follows: solid circles, 10349 cells (I=DD; II=DD) stimulated by York cells against York targets (York is mismatched for 10349 at I and II); solid squares, 10349 cells stimulated by CC (I=CC; II=CC) against CC targets; solid triangles, 10349 cells stimulated by CC against GG (I=CC; II=DD) targets; open triangles, 10349 cells stimulated by GG against GG targets; open circles, 10349 cells stimulated by GG against CC targets; open squares, 10349 cells stimulated by York against DD (I=DD; II=DD). The genotypes in the right panel (rejecting animal) are as follows: solid circles, 10348 cells stimulated by York against York; solid squares, 10348 cells stimulated by CC against CC; solid triangles, 10348 cells stimulated by CC against GG; open squares, 10348 cells stimulated by GG against GG; open squares, 10348 cells stimulated by York against DD.
Figure 3:
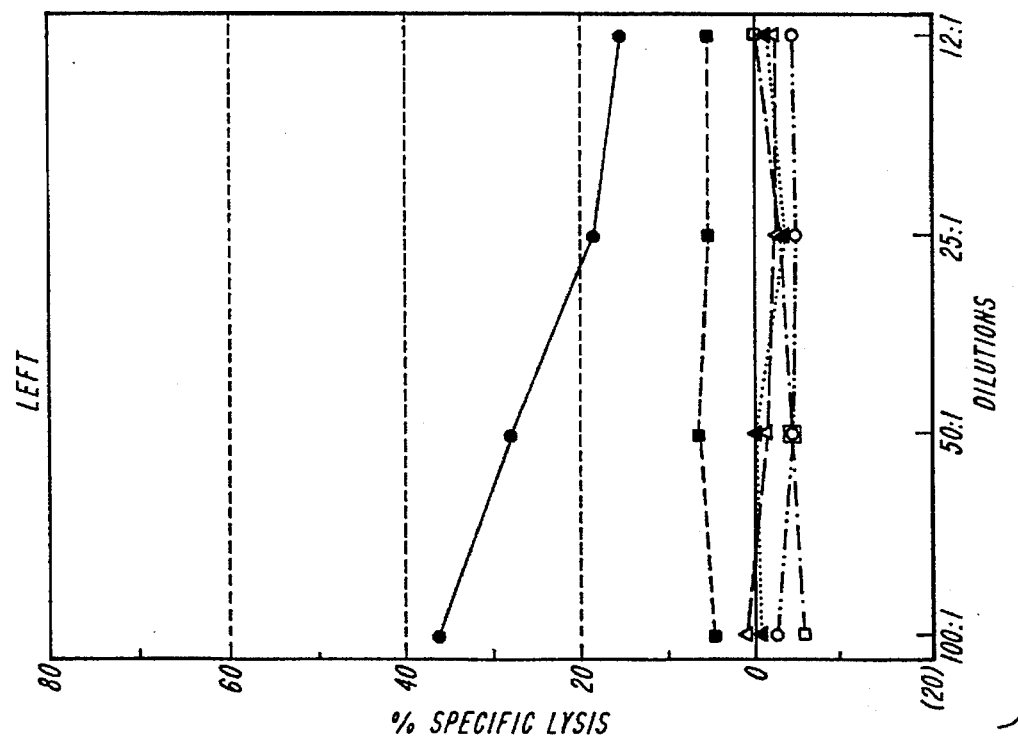

FIG. 3 shows the classical cytotoxic reactivity of tolerant and rejecting animals. The tolerant animals do not react against donor type cells (GG) or against cells bearing the same class I marker(C) after stimulation by GG or CC but third party reactivity is maintained. The rejecting animals, however, react strongly against donor type cells and donor class I matched cells and often higher than a third party (outbred) response emphasizing the immunization.

The expression of IL-10 in grafts received by tolerant and rejecting animals was followed by northern analysis. IL-10 was present at a higher level in the grafted organs of tolerant animals than in the grafted organs of rejecting animals. Higher levels of IL-10 in the transplanted organs of tolerant animals was seen beginning on about day eight. IL-10 was detectable in grafts in tolerant animals up to and beyond day 18 post-transplant. In tolerant animals, no other cytokines detectable in rejecting animals or otherwise thought to be involved in rejection were detected. However, in addition to IL-10, expression of IL-1β and IL-6 were also detected. One tolerant animal presented a temporary increase of creatinine (at day 18, 6 days after stopping the CyA). In our model, IL-1β and IL-6 are generally expressed late and strongly in rejecting animals; however, this expression is non specific since we can detect these cytokines in tolerant animals as well, but transiently and at a much lower level than in rejected organs. IL-10 was also detectable in rejecting animals at a very low level with a maximum of expression at a late stage of the rejection. IFN-γ, TNF-α, were detected in rejecting animals.

RNA extractions for cytokine mRNA analysis were performed as follows. Renal tissue wedges of between 100 and 200 grams were obtained by open biopsies at different time points post-transplantation, immersed in 3 ml of 4M guanidine thiocyanate (GuSCN) with 2% 2-ME (mercaptoethanol) and immediately frozen in liquid nitrogen. After homogenisation with a tissue homogenizer (Omni International), the samples were centrifuged at 3,0009 to pellet tissue debris. Total RNA was pelleted through a CsCl gradient (5.7M CsCl, 25 mM Na Citrate) 3 ml of GuSCN was overlain 1.2 ml CsCl and centrifuged at 42,000 rpm at 15° C. for 14 hours in a Beckman ultracentrifuge L8-80M (Palo Alto, Calif.). The supernatants were removed and the pellets washed with 70% ethanol and dried at room temperature. The pellets were resuspended in 200 µl of diethylpyrocarbonate treated Tris EDTA (TE) 1×. After phenol extraction, the RNA samples were precipitated in ethanol and finally resuspended in TE 1× buffer. The concentration of RNA was determined by absorbence at 260 nm.

Northern blot analysis was performed as follows. 20 µg of RNA (denatured at 65° C. for 5 minutes) were loaded on formaldehyde 1.2% agarose gels, stained with ethidium bromide, and run overnight at 22 volts. The ethidium bromide staining allowed assessment of the integrity of RNA. After migration, the gels were washed in distilled water twice for 10 minutes and then placed in 10× SSC for one hour. The gels were then blotted by capillarity on Zetaprobe membranes (Bio-Rad) using 10× SSC buffer as a blotting solution. After blotting, the membranes were cross-linked in a UV Stratalinker (Stratagene) by exposure to 1200 µwatts/cm. The filters were prehybridized for at least 4 hours in 10% dextran sulfate, 4× SSC, 40% Formaldehyde, 5× Denhardt's, 0.5% SDS, 20 µg/ml salmon sperm DNA, and then hybridized to $^{32}P$ labeled probes in the same solution at 42° C. for 14 hours. The probes were labeled with $^{32}P$ dATP and dCTP to a specific activity about $10^9$ cpm/µg using a random priming kit (Promega). The filters were than washed twice in 2× SSC at room temperature for 10 minutes and twice in 0.1× SSC at 60° C. for 25 minutes. The filters were then exposed to films in cassettes for a period of 4 to 10 days. After developing, the films were scanned in a Computing Densitometer (Molecular Dynamics). Since a glyceraldehyde phosphodehydrogenase (GAPDH) probe was used to assess the amount of RNA loaded, the IL-10 transcripts levels presented were always normalized with GAPDH values.

Pigs selected were from a herd of partially inbred miniature swine (NIH minipigs) at 5 to 7 months of age. The genetic characteristics of this herd have been described in previous publications (Pescovitz et al., (1983) Transplant Proc. 15, 1124; Pescovitz et al., (1984)*J. Exp. Med.* 160, 1495). The intra-MHC recombinant haplotype g (class Icc, class IIdd) allows transplants to be performed across isolated class I disparities. Long term tolerance in transplants with a combination of 2 class I disparities between donor and recipient, was induced by administration of CyA 10 mg/kg/day for 12 days. Untreated animals subjected to the same graft rejected within 8 to 11 days. Three control and three CyA animals were tested. All procedures were performed in accordance with "The guide for the Care and Use of Laboratory Animals", published by the National Institute of Health (NIH Publication 85-23, revised 1985) and were approved by the National Cancer Institute Animal Research Committee. Orthotopic kidney grafts were performed as previously described (Kirkman et al., (1979)*Transplantation* 28, 18).

Cellular assays were performed as previously described, see, e.g., (Kortz et al., (1990) *Transplantation* 49, 1142). Briefly, one-way mixed lymphocyte cultures were prepared using 24-wells, flat-bottomed plates (Costar, Cambridge, Mass.) containing 4×10⁶ responder and 4×10⁶ stimulator PBL per well in 2 ml of medium. Stimulator cells were irradiated (25 Gy) with a cesium source prior to plating. Cultures were incubated for 6 days at 37° C. in 8% $CO_2$ and 100% humidity. Effector cells were harvested from bulk cultures and were tested on lymphoblast targets prepared by culturing 3×10⁷ PBL in 5 ml of medium containing 10 µl of phytohemagglutinin (M-Form, Gibco) for 24 hours. Targets were labeled with 51Cr (Amersham, Arlington Heights, Ill.) and were then plated on 96-well round-bottomed plates (Costar) along with effector cells. In all experiments, effector cells were tested on two different specific targets (target cells MHC matched or class I matched to stimulators) and one negative target (target cells MHC matched to effectors). The tests were run in triplicate at four different effector:target ratios (100:1, 50:1, 25:1, 12.5:1) and were incubated for 5 to 6 hours. Supernatants were harvested using the SkatronSupernatant Collection System (Skatron, Sterling, Va.) and 51Cr release was determined on a gamma counter (Micromedics, Huntsville, Ala.). Maximum lysis was obtained with the nonionic detergent NP-40 (BRL, Rockville, Md.). The results were expressed as % specific lysis:

$$= \frac{\text{experimental release (cpm)} - \text{spontaneous release (cpm)}}{\text{maximal release (cpm)} - \text{spontaneous release (cpm)}} \times 100$$

Discordant Xenograft

The following procedure was designed to lengthen the time an implanted organ (a xenograft) survives in a xenogeneic host prior to rejection. The organ can be any organ, e.g., a liver, e.g., a kidney, e.g., a heart. The main strategies are removal of natural antibodies, e.g., by organ perfusion, transplantation of tolerance-inducing cells, e.g., donor species bone marrow cells or cells, recipient species or recipient cells transduced with DNA encoding a donor MHC gene, or donor thymic tissue, the implantation of donor stromal tissue, the administration of a short course of a help reducing agent at about the time of introduction of the graft, and the administration of a cytokine, e.g., IL-10, which enhances tolerance or inhibits GVHD. Preparation of the recipient for transplantation includes any or all of these steps. Preferably, they are carried out in the following sequence.

First, a preparation e.g., horse, anti-human thymocyte globulin (ATG) is intravenously injected into the recipient. The antibody preparation eliminates mature T cells and natural killer cells. If not eliminated, mature T cells would promote rejection of both the bone marrow transplant and, after sensitization, the xenograft itself. Of equal importance, the ATG preparation also eliminates natural killer (NK) cells. NK cells probably have no effect on the implanted organ, but would act immediately to reject the newly introduced bone marrow. In the case of a human recipient, anti-human ATG obtained from any mammalian host can also be used, e.g., ATG produced in pigs, although thus far preparations of pig ATG have been of lower titer than horse-derived ATG. ATG is superior to anti-NK monoclonal antibodies, as the latter are generally not lytic to all host NK cells, while the polyclonal mixture in ATG is capable of lysing all host NK cells. Anti-NK monoclonal antibodies can, however, be used.

The presence of donor antigen in the host thymus during the time when host T cells are regenerating post-transplant can be critical for tolerizing host T cells. If donor hematopoietic stem cells are not able to become established in the host thymus and induce tolerance before host T cells regenerate repeated doses of anti-recipient T cell antibodies may be necessary throughout the non-myeloablative regimen. Continuous depletion of host T cells may be required for several weeks. Alternatively, e.g., if this approach is not successful, and tolerance (as measured by donor skin graft acceptance) is not induced in these animals, the approach can be modified to include host thymectomy. In thymectomized recipients, host T cells do not have an opportunity to differentiate in a host thymus, but must differentiate in the donor thymus. Immunocompetence can be measured by the ability to reject a non-donor type allogeneic donor skin graft, and to survive in a pathogen-containing environment.

It may also be necessary or desirable to splenectomize the recipient in order to avoid anemia.

Second, the recipient is administered low dose radiation in order to create hematopoietic space for a newly injected bone marrow cells. A sublethal dose of between 100 rads and 400 rads whole body radiation is suitable.

Additionally, 700 rads of local thymic radiation is effective for destroying residual T cells.

Third, natural antibodies are absorbed from the recipient's blood by contacting them with antigen, e.g., donor species antigen, e.g., by hemoperfusion of a liver of the donor species. Preformed natural antibodies (mAb) are the primary agents of graft rejection. Natural antibodies bind to xenogeneic endothelial cells and are primarily of the IgM class. These antibodies are independent of any known previous exposure to antigens of the xenogeneic donor. B cells that produce these natural antibodies tend to be T cell-independent, and are normally tolerized to self antigen by exposure to these antigens during development. The mechanism by which newly developing B cells are tolerized is unknown. The liver is a more effective absorber of natural antibodies than the kidney.

The fourth step in the non-myeloablative procedure is to implant donor stromal tissue, preferably obtained from fetal or neonatal liver, thymus, and/or fetal spleen, into the recipient, preferably in the kidney capsule. Stem cell engraftment and hematopoiesis across disparate species barriers is enhances by providing a hematopoietic stromal environment from the donor species. The stromal matrix supplies species-specific factors that are required for interactions between hematopoietic cells and their stromal environment, such as hematopoietic growth factors, adhesion molecules, and their ligands. "Stromal tissue," as used herein, refers to the supporting tissue or matrix of an organ, as distinguished from its functional elements of parenchyma.

As liver is the major site of hematopoiesis in the fetus, fetal liver can also serve as an alternative to bone marrow as a source of hematopoietic stem cells. The thymus is the major site of T cell maturation. Each organ includes an organ specific stromal matrix that can support differentiation of the respective undifferentiated stem cells implanted into the host. Although adult thymus may be used, fetal tissue obtained sufficiently early in gestation is preferred because it is free from mature T lymphocytes which can cause GVHD. Fetal tissues also tend to survive better than adult tissues when transplanted. As an added precaution against GVHD, thymic stromal tissue can be irradiated prior to transplantation, e.g., irradiated at 1000 rads, or a cytokine, preferably a donor species cytokine, which inhibits donor cell response against the host, e.g., IL-10, preferably donor species IL-10 can be administered. As an alternative or an adjunct to implantation, fetal liver cells can be administered in fluid suspension.

Fifth, an appropriate source of tolerizing donor antigen, e.g., bone marrow cells (BMC), or another source of hematopoietic stem cells, e.g., a fetal liver suspension, of the donor are administered to, e.g., injected into, the recipient. Donor BMC home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. When an organ graft is placed in such a recipient at or after bone marrow chimerism has been induced, natural antibody against the donor will have been minimized and the graft would be accepted by both the humoral and the cellular arms of the immune system. This approach has the added advantage of permitting organ transplantation to be performed sufficiently long following transplant of hematopoietic cells, e.g., BMT, e.g., a fetal liver suspension, that normal health and immunocompetence will have been restored at the time of organ transplantation. The use of xenogeneic donors allows the possibility of using bone marrow cells and organs from the same animal, or from genetically matched animals.

Alternatively, donor antigen can be provided by recipient species cells genetically engineered to express donor antigen. Retroviral transformation allows the reconstitution of a graft recipient's bone marrow with transgenic bone marrow cells, preferably autologous bone marrow cells, expressing allogeneic or xenogeneic MHC genes. Expression of the transgenic MHC genes confers tolerance to grafts which exhibit the products of these or closely related MHC genes. Thus, these methods provide for the induction of specific transplantation tolerance by somatic transfer of MHC genes.

Alternatively, xenogeneic (donor species) thymic tissue can be introduced into the recipient to induce tolerance. Preferably, the recipient is thymectomized or otherwise treated to suppress host thymic function.

Prior to implantation, the organ to be transplanted is perfused with IL-10. Recipient species IL-10, or IL-10 specific to a species relatively closely related to the host is most useful in promoting tolerance. Donor species IL-10 can act to inhibit graft antigen presenting cells, and thus render the graft less immunogenic with minimal effects on the host. Additionally, the presence of IL-109 without co-stimulation of T cells may anergize T cells. Donor species IL-10, or IL-10 from a relatively closely related species is most useful in inhibiting GVHD. It is preferable to use both forms of IL-10 to simultaneously promote tolerance and inhibit GVHD.

Finally, a short course of a help reducing agent, e.g., a short course of high dose CsA is administered to the recipient. As is described herein, the course is begun at about the time of implantation, or a little before, and is continued for a time about equal to the time it takes for a mature T cell to be stimulated and initiate rejection. The duration of the short course of help reducing treatment, e.g., cyclosporine administration, should be approximately equal to or less than the period required for mature T cells of the recipient species to initiate rejection of an antigen after first being stimulated by the antigen (in humans this is usually 8–12 days, preferably about 10 days).

In the case of xenogeneic grafts, the donor of the implant and the individual that supplies either the tolerance-inducing hematopoietic cells or the liver to be perfused should be the same individual or should be as closely related as possible. For example, it is preferable to derive implant tissue from a colony of donors that is highly inbred.

While any of these procedures may aid the survival of an implanted organ, best results are achieved when all steps are used in combination.

Detailed Protocol

A protocol for preparing a cynomolgus monkey for receipt of a kidney from a miniature swine donor is presented below.

Cynomolgus monkeys can be purchased from Charles River Research Laboratories. The animals should be quarantined, tested for pathogens, and housed in environmentally controlled rooms in conformance to the N.I.H. Guide for Care and use of Laboratory Animals, in a AAALAC accredited facility. Animals can be typed by a standard complement mediated cytotoxicity assay for Class I antigens and by MLC nonreactivity for Class II matching. Renal function can be followed by creatinine and BUN levels in serum. Pathology was by biopsy. Biopsies were performed at day 7, then weekly for 2 months, then monthly. Zero time is defined as the moment that the arterial and venous cannulas of the recipient are connected to the liver to be perfused.

On day -1 a commercial preparation (Upjohn) of horse anti-human anti-thymocyte globulin (ATG) is injected into the recipient. ATG eliminates mature T cells and natural killer cells that would otherwise cause rejection of the bone marrow cells used to induce tolerance. The recipient is anesthetized, an IV catheter is inserted into the recipient, and 6 ml of heparinized whole blood are removed before injection. The ATG preparation is then injected (50 mg/kg) intravenously. Six ml samples of heparinized whole blood are drawn for testing at time points of 30 min., 24 hrs and 48 hrs. Blood samples are analyzed for the effect of antibody treatment on natural killer cell activity (testing on K562 targets) and by FACS analysis for lymphocyte subpopulations, including CD4, CD8, CD3, CD11b, and CD16. Preliminary data from both assays indicate that both groups of cells are eliminated by the administration of ATG. If mature T cells and NK cells are not eliminated, ATG can be re-administered at later times in the procedure, both before and after organ transplantation.

Sublethal irradiation is administered to the recipient between days -1 and -8. Irradiation is necessary to eliminate enough of the recipient's endogenous BMC to stimulate hematopoiesis of the newly introduced foreign MBC. Sublethal total body irradiation is sufficient to permit engraftment with minimal toxic effects to the recipient. Whole body radiation (150 Rads) was administered to cynomolgus monkey recipients from a bilateral (TRBC) cobalt teletherapy unit at 10 Rads/min. Local irradiation of the thymus (700 Rads) was also employed in order to facilitate engraftment.

Natural antibodies are a primary cause of organ rejection. To remove natural antibodies from the recipient's circulation prior to transplantation, on day 0 an operative absorption of natural antibodies (mAb) is performed, using a miniature swine liver, as follows. At -90minutes the seine donor is anesthetized, and the liver prepared for removal by standard operative procedures. At -60 minutes the recipient monkey is anesthetized. A peripheral IV catheter is inserted, and a 6 ml sample of whole blood is drawn. Through mid-line incision, the abdominal aorta and the vena cava are isolated. Silastic cannulas containing side ports for blood sampling are inserted into the blood vessels.

In advance of transplantation, the donor organ is perfused with IL-10. Porcine IL-10 will be most useful in down regulating the graft's immune responsive to the host (GVHD).

At about -4 hours the short course of help suppression is started. An intravenous preparation of CsA (Sandimmune, i.v.) can be obtained from Sandoz Pharmaceuticals Corporation, Hanover, N.J. and is suitable for use in the methods of the invention. Monkeys should receive about 12 doses of about 10 mg/kg with the first dose given 4 hours prior to graft revascularization. The CsA can be diluted in 250 ml of normal saline and infused intravenously over 1 hour. The CsA should be administered without other immunosuppressants. The duration of therapy should be about 12 days. The suitable dosage in pigs is about 15 mg/kg delivered intramuscularly. The dosage in either animal should be such that a blood level of about 500–1,000 ng/ml is maintained.

At -30 minutes the liver is perfused in situ until it turns pale, and then removed from the swine donor and placed into cold Ringers Lactate. The liver is kept cold until just prior to reperfusion in the monkey. A liver biopsy is taken. At -10 minutes the liver is perfused with warm albumin solution until the liver is warm (37 degrees).

At 0 time the arterial and venous cannulas of the recipient are connected to the portal vein and vena cava of the donor liver and perfusion is begun. Liver biopsies are taken at 30 minutes and 60 minutes, respectively. Samples of recipient blood are also drawn for serum at 30 minutes and 60 minutes respectively. At 60 minutes the liver is disconnected from the cannulas the recipient's large blood vessels are repaired. The liver, having served its function of absorbing harmful natural antibodies from the recipient monkey, is discarded. Additional blood samples for serum are drawn from the recipient at 2, 24, and 48 hours.

To promote long-term survival of the implanted organ through T cell and B cell mediated tolerance, donor bone marrow cells are administered to the recipient to form chimeric bone marrow. The presence of donor antigens in the bone marrow allows newly developing B cells, and newly sensitized T cells, to recognize antigens of the donor as self, and thereby induces tolerance for the implanted organ tissue, in the form of tissue slices of fetal liver, thymus, and/or fetal spleen are transplanted under the kidney capsule of the recipient. Stromal tissue is preferably implanted simultaneously with, or prior to, administration of hematopoietic stem cells, e.g., BMC, or a fetal liver cell suspension.

To follow chimerism, two color flow cytometry can be used. This assay uses monoclonal antibodies to distinguish between donor class I major histocompatibility antigens and leukocyte common antigens versus recipient class I major histocompatability antigens.

BMC can in turn be injected either simultaneously with, or preceding, organ transplant. Bone marrow is harvested and injected intravenously ($7.5 \times 10^8$/kg) as previously described (Pennington et al., 1988, *Transplantation* 45:21–26). Should natural antibodies be found to recur before tolerance is induced, and should these antibodies cause damage to the graft, the protocol can be modified to permit sufficient time following BMT for humoral tolerance to be established prior to organ grafting.

The approaches described above are designed to synergistically prevent the problem of transplant rejection. Use The peptides of the invention may be administered to a mammal, particularly a mammal, particularly a human, in one of the traditional modes (e.g., orally, paternally, transdermally, or transmucosally), in a sustained release formulation using a biodegradable biocompatible polymer, or by on-site delivery using micelles, pumps, e.g., osmotic drug delivery pumps, gels and liposomes or by transgeneic modes.

Other Embodiments

Included in the invention are: allelic variations; natural mutants; induced mutants; proteins encoded by DNA that hybridizes under high or low stringency conditions to a nucleic acid which encodes the peptide of (SEQ ID NO:1) (for definitions of high and low stringency see Current Protocols in Molecular Biology, John Wiley & Sons, New York, 1989, 6.3.1–6.3.6, hereby incorporated by reference); and, peptides or proteins specifically bound by antisera to porcine IL-10, especially by antisera to an active site or binding domain of porcine IL-10, e.g., antisera to an epitope active in binding to an IL-10 receptor e.g., antigen which blocks the binding of nature porcine IL-10 with IL-10 receptor-bearing cells. Also included are chimeric porcine IL-10s that include a porcine IL-10 peptide or protein and a second peptide, e.g., a toxin, e.g., a chimeric molecule which includes the IL-10-receptor binding portion of IL-10 and a toxic fragment of diphtheria toxin.

The invention also includes biologically active fragments or analogs of porcine IL-10. A biologically active fragment or analog is one having any in vivo in vitro activity which is characteristic of the porcine IL-10 shown in (SEQ ID NO:1) e.g., one or more of the biological activities described above). Because peptides such as porcine IL-10 often exhibit a range of physiological properties and because such properties may be attributable to different portions of the molecule, a useful porcine IL-10 fragment or porcine IL-10 analog is one which exhibits a biological activity in any biological assay for porcine IL-10 activity. Most preferably the fragment or analog possesses 10%, preferably 40%, or at least 90% of the activity of porcine IL10 (SEQ ID NO:1), in any in vivo in vitro porcine IL-10 assay.

Analogs can differ from naturally occurring porcine IL-10 in amino acid sequence or in ways that do not involve sequence, or both. Analogs of the invention will generally exhibit at least 90%, preferably 95% or even 99%, homology with a segment of 20 amino acid residues, preferably more than 40 amino acid residues, or more preferably the entire sequence of a naturally occurring porcine IL-10 sequence. Non-sequence modifications include in vivo or in vitro chemical derivatization of porcine IL-10s. Non-sequence modifications include changes in acetylation, methylation, phosphorylation, carboxylation, or glycosylation. Glycosylation can be modified, e.g., by modifying the glycosylation patterns of a porcine IL-10 during its synthesis and processing or in further processing steps, e.g., by exposing the porcine IL-10 to glycosylation affecting enzymes derived from cells that normally provide such processing, e.g., mammalian glycosylation enzymes; phosphorylation can be modified by exposing the porcine IL-10 to phosphorylation-altering enzymes, e.g., kinases or phosphatases.

Preferred analogs include porcine IL-10 (or biologically active fragments thereof) whose sequences differ from the wild-type sequence by one or more conservative amino acid substitutions or by one or more non-conservative amino acid substitutions, deletions, or insertions which do not abolish the porcine IL-10's biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

| CONSERVATIVE AMINO ACID REPLACEMENTS | | |
|---|---|---|
| For Amino Acid | Code | Replace with any of |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S—Me—Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S—Me—Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

In addition to substantially full-length porcine IL-10s, the invention also includes biologically active fragments of the porcine IL-10s. As used herein, the term "fragment", as applied to a porcine IL-10, will ordinarily be at least about residues, more typically at least about 40 residues, preferably at least about 60 residues in length. Fragments of porcine IL-10 can be generated by methods known to those skilled in the art. The ability of a candidate fragment to exhibit a biological activity of porcine IL-10 can be assessed by methods known to those skilled in the art as described herein. Also included are porcine IL-10's containing residues that are not required for biological activity of the peptide or that result from alternative mRNA splicing or alternative protein processing events.

Also within the invention are: a nucleic acid which encodes a protein or peptide of the invention; and, a purified antibody preparation, preferably a monoclonal antibody preparation, directed against a protein or peptide of the invention.

Nucleic acid encoding all or part of the porcine IL-10 gene can be used to transform cells. For example, the procine IL-10 gene, e.g., a mis-expressing or mutant form of it e.g., a deletion, or other DNA encoding an IL-10 protein or peptide can be used to transform a cell and to produce a cell in which the cell's genomic porcine IL-10 gene has been replaced by the transformed gene, producing, e.g., a cell deleted for the IL-10 gene. This approach can be used with cells capable of being grown in culture, e.g., cultured stem cells, to investigate the function of the gene.

Analogously, nucleic acid encoding all or part of the porcene IL-10 gene, e.g., a mis-expressing or mutant form of the gene, e.g., a deletion, can be used to transform a cell which subsequently gives rise to a transgenic animal, e.g. a transgeneic swine. This approach can be used to crate, e.g., a transgenic animal in which the porcine IL-10 gene is, e.g., inactivated, e.g., by a deletion. Homozygous transgenic animals can be made by crosses between the offspring of a founder transgenic animal. Cell or tissue cultures can be derived from a transgenic animal.

In order to obtain a porcine IL-10 peptide porcine IL-10 encoding DNA is introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-porcene IL-10 antibodies by prior art methods.

Fragments of IL-10 can be made by expressing IL-10 DNA which has been manipulated in vitro to encode the desired fragment; e.g., by restriction digestion of the DNA sequence of SEQ ID NO:1. Analogs can be made, e.g., by in vitro DNA sequence modifications of the sequence of SEQ ID NO:1. For example, in vitro mutagenesis can be used to convert the DNA sequence of SEQ ID NO:1 into a sequence which encodes an analog in which one or more amino acid residues has undergone a replacement, e.g., a conservative replacement as described in table 1. Fragments or analogs can be tested by methods known to those skilled in the art for the presence of IL-10 activity.

Other embodiments are within the following claims.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1365 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGCACGAGCA  GGGGCTTGCC  CTTGCAAAAC  CAAACCACAA  GTCCGACTCA  ACGAAGAAGG                60

CACAGCTCTA CC ATG CCC AGC TCA GCA CTG CTC TAT TGC CTG ATC TTC                        108
              Met Pro Ser Ser Ala Leu Leu Tyr Cys Leu Ile Phe
               1           5                       10

CTG GCA GGG GTG GCA GCC AGC ATT AAG TCT GAG AAC AGC TGC ATC CAC                      156
Leu Ala Gly Val Ala Ala Ser Ile Lys Ser Glu Asn Ser Cys Ile His
            15              20                  25

TTC CCA ACC AGC CTG CCC CAC ATG CTC CGG GAA CTC CGA GCT GCC TTC                      204
Phe Pro Thr Ser Leu Pro His Met Leu Arg Glu Leu Arg Ala Ala Phe
        30                  35              40

GGC CCA GTG AAG AGT TTC TTT CAA ACG AAG GAC CAG ATG GGC GAC TTG                      252
Gly Pro Val Lys Ser Phe Phe Gln Thr Lys Asp Gln Met Gly Asp Leu
45                   50                 55                   60

TTG CTG ACC GGG TCT CAG CTG GAG GAC TTT AAG GGT TAC CTG GGT TGC                      300
Leu Leu Thr Gly Ser Gln Leu Glu Asp Phe Lys Gly Tyr Leu Gly Cys
                65                  70                  75

CAA GCC TTG TCA GAG ATG ATC CAG TTT TAC CTG GAA GAC GTA ATG CCG                      348
Gln Ala Leu Ser Glu Met Ile Gln Phe Tyr Leu Glu Asp Val Met Pro
            80                  85                  90

AAG GCA GAG AGT GAT GGG GAG GAT ATC AAG GAG CAC GTG AAC TCC CTG                      396
Lys Ala Glu Ser Asp Gly Glu Asp Ile Lys Glu His Val Asn Ser Leu
        95                  100                 105

GGG GAG AAG CTG AAG ACC CTC AGG CTG AGG CTG CGG CGC TGT CAT CAA                      444
Gly Glu Lys Leu Lys Thr Leu Arg Leu Arg Leu Arg Arg Cys His Gln
    110                 115                 120

TTT CTG CCC TGT GAA AAC AAG AGC AAG GCC GTG GAG GAG GTG AAG AGT                      492
```

| | | | | | | | | | | | | | | | | |
|---|---|---|---|---|---|---|---|---|---|---|---|---|---|---|---|---|
| Phe | Leu | Pro | Cys | Glu | Asn | Lys | Ser | Lys | Ala | Val | Glu | Glu | Val | Lys | Ser | |
| 125 | | | | 130 | | | | | 135 | | | | | 140 | | |

| | | | | | | | | | | | | | | | |
|---|---|---|---|---|---|---|---|---|---|---|---|---|---|---|---|
| GCC | TTT | AGC | AAG | CTC | CAA | GAG | AGG | GGT | CTC | TAC | AAA | GCC | ATG | GGT | GAG | 540 |
| Ala | Phe | Ser | Lys | Leu | Gln | Glu | Arg | Gly | Leu | Tyr | Lys | Ala | Met | Gly | Glu | |
| | | | | 145 | | | | | 150 | | | | | 155 | | |

| | | | | | | | | | | | | | | | |
|---|---|---|---|---|---|---|---|---|---|---|---|---|---|---|---|
| TTT | GAC | ATC | TTC | ATC | AAC | TAC | ATA | GAA | GCC | TAC | ATG | ACG | ATG | AAG | ATG | 588 |
| Phe | Asp | Ile | Phe | Ile | Asn | Tyr | Ile | Glu | Ala | Tyr | Met | Thr | Met | Lys | Met | |
| | | | | 160 | | | | | 165 | | | | | 170 | | |

| | | | | | | |
|---|---|---|---|---|---|---|
| AGG | AAG | AAC | TGAAGCATTC | TAGGGAAACC | AAAGAAAAAC | CTTCCAGGAT | 637 |
| Arg | Lys | Asn | | | | | |
| | | 175 | | | | | |

```
GACGACTCTA    CTAAACTCTA    GGATACAAAT    TGGAGACTTT    CAAAATCTGC    TCCAAGGTTC         697

CCGGGGAGCA    GAACCAGCAC    CCTGGGAAAC    CCTGCTGTAC    CTCTCCCCTG    AGATATTTAT         757

TACCTCTGAT    ACCTCAGCTC    CCATTTCTAT    TTATTTACCG    AGCCTCTCTG    TGAACTATTT         817

AGAAGAAGAA    CAGTATTATA    CTTTTTTCAG    TATTTATTAT    TTCACCTGT     GTTAAGCTT          877

TCCATAGGGT    GTGCCCTATG    GTGTTCAACT    GTTTAAGAG     AAATTGTAAG    TTATATAAGG         937

GGGGAAAAAA    TGTTCCTTCA    GGAGCCAACT    GCAGCTTCCA    TTCCAAGCCT    ACCCACCCGG         997

GAAAGCTAGT    GGGCTATTTG    TCCTGACTGC    CTCCACTTT     CTCTTGTCCC    TGGGCTGGGG        1057

CTTCCGGAGT    GTGACAAAGT    CGTTTACACT    CATAGGAAGA    GAAACTAGGG    AGCCCCTTTG        1117

ACAGCTAATA    TTCCGGTGGC    CCTGAGGGAT    TCCCCTGACC    TCATTCCCCA    AACACTTCAT        1177

TCTTGAAAGC    TGTGGCCAGC    TTGTTATTTA    AACAACCTA     AAATTGGTTC    TAATAGAACT        1237

CGGTTTTAAC    TAGAAGCAAT    TCAATTCCTC    TGGGAATGTT    ACATTGTTTG    TCTGTCTTCA        1297

TAGCAGATTT    TAATTTTGAA    TAAATAAATG    GTCTTATTCA    AAAAAAAAA     AAAAAAAAA         1357

AAAAAAA                                                                                1365
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

TTAAGGGTTA CTTGGGTT                                                                                                  18

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TTNCW Y TTRT T Y TCRCANG                                                                  19

We claim:

1. Purified DNA comprising a sequence which encodes a peptide having at least 90% sequence similarity with the peptide from SEQ ID NO:1 and said peptide having a porcine IL-10 activity, said activity being chosen from the group of: inhibiting the ability of T cells to release or produce IL-2 when administered to T cells; inhibiting the ability of T cells to release or produce gamma interferon when administered to T cells; and competitively inhibiting the binding of IL-10 to cells.

2. The purified DNA of claim 1, wherein said encoded peptide has at least 95% sequence similarity with the peptide of SEQ ID NO:1.

3. The purified DNA of claim 1, wherein said encoded peptide has at least 98% sequence similarity with the peptide of SEQ ID NO:1.

4. The purified DNA of claim 1, wherein said DNA encodes the peptide sequence of SEQ ID NO:1.

5. Purified DNA comprising a sequence encoding a peptide of 30 or more amino acids in length said peptide being a fragment of SEQ ID NO:1.

6. The purified DNA sequence of claim 5, wherein said DNA encodes a peptide which is at least 40 amino acids in length.

7. The purified DNA sequence of claim 5, wherein said DNA encodes a peptide which is at least 50 amino acids in length.

8. The purified DNA sequence of claim 5, wherein said DNA encodes a peptide which is at least 60 amino acids in length.

9. The purified DNA sequence of claim 5, wherein said DNA encodes a peptide which is at least 80 amino acids in length.

10. The purified DNA sequence of claim 5, wherein said DNA encodes a peptide which is at least 100 amino acids in length.

11. The purified DNA sequence of claim 5, wherein said DNA encodes a peptide which is at least 120 amino acids in length.

12. A vector comprising the purified DNA sequence of claim 1.

13. A host cell containing the purified DNA of claim 1.

14. The cell of claim 13, wherein said host cell is capable of expressing a peptide having porcine IL-10 activity.

15. An essentially homogenous population of host cells, each of which comprises the purified DNA of claim 1 or 5.

16. A method for manufacture of peptide having porcine IL-10 activity comprising culturing the host cell of claim 13 in a medium to express said peptide.

17. The purified DNA of claim 1, wherein said encoded peptide has at least 99% sequence similarity with the peptide of SEQ NO:1.

18. A vector comprising the purified DNA sequence of claim 5.

19. A host cell containing the purified DNA of claim 5.

20. The host cell of claim 19, wherein said cell is capable of expressing a peptide which is a fragment at least 30 amino acids long of the peptide of SEQ ID NO:1.

21. A method for manufacture of a peptide which is a fragment at least 30 amino acids long of the peptide of SEQ ID NO:1 comprising culturing the host cell of claim 20 in a medium to express said peptide.

22. The purified DNA of claim 1, wherein said peptide has the activity of inhibiting the ability of T cells to release or produce IL-2 when administered to T cells.

23. The purified DNA of claim 1, wherein said peptide has the activity of inhibiting the ability of T cells to release or produce gamma interferon when administered to T cells.

24. The purified DNA of claim 1, wherein said peptide has the activity of competitively inhibiting the binding of IL-10 to cells.

25. The purified DNA of claim 24, wherein said peptide has the activity of competitively inhibiting the binding of porcine IL-10 to porcine T cells.

26. Purified DNA comprising a sequence which encodes the peptide of SEQ ID NO:1.

27. Purified DNA which comprises the nucleic acid sequence of SEQ ID NO:1.

* * * * *